United States Patent [19]

Blaszkiewicz et al.

[11] Patent Number: 5,130,119
[45] Date of Patent: Jul. 14, 1992

[54] METHOD OF USING FLUOROSUBSTITUTED BENZENE DERIVATIVES IN F-NMR IMAGING

[75] Inventors: Peter Blaszkiewicz; Ulrich Niedballa; Heinz Gries; Hans Bauer; Hanns-Joachim Weinmann, all of Berlin, Fed. Rep. of Germany

[73] Assignee: Schering Aktiengesellschaft, Berlin & Bergkamen, Fed. Rep. of Germany

[21] Appl. No.: 417,946

[22] Filed: Oct. 6, 1989

[30] Foreign Application Priority Data

Oct. 7, 1988 [DE] Fed. Rep. of Germany ....... 3834704

[51] Int. Cl.⁵ ............... A61N 49/00; A01N 37/28; A01N 37/10; C07C 315/00
[52] U.S. Cl. ........................... 424/9; 514/507; 514/532; 514/542; 514/562; 514/576; 562/430
[58] Field of Search .................. 424/9; 514/562, 507, 514/532, 542, 576; 562/430

[56] References Cited

U.S. PATENT DOCUMENTS

| | | | |
|---|---|---|---|
| 3,920,444 | 11/1975 | Harrington et al. | 71/103 |
| 4,766,243 | 8/1988 | Fifolt | 564/414 |
| 4,804,529 | 2/1989 | Bardy et al. | 424/9 |
| 4,859,449 | 10/1989 | Mattes | 424/9 |

FOREIGN PATENT DOCUMENTS

| | | |
|---|---|---|
| 718129 | 7/1968 | Belgium . |
| 1917821 | 11/1969 | Fed. Rep. of Germany . |
| 1579473 | 8/1969 | France . |

OTHER PUBLICATIONS

Trepka, R. D., et al., J. Agr. Food Chem. 22, Nr. 6, pp. 1111-1119 (1974).
Deutsch, C. J., et al., Annals N.Y. Acad. Sci. 508, pp. 33-46 (1987).

*Primary Examiner*—Frederick E. Waddell
*Assistant Examiner*—T. J. Criares
*Attorney, Agent, or Firm*—Millen, White & Zelano

[57] ABSTRACT

Fluorosubstituted benzene derivatives of Formula I

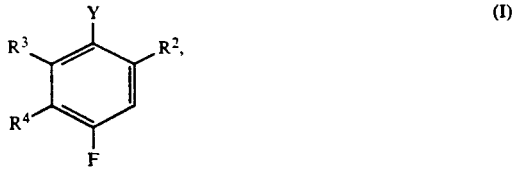

wherein
Y, $R^2$, $R^3$ and $R^4$ are defined herein, are NMR diagnostic agents.

26 Claims, 4 Drawing Sheets

METHOD OF USING FLUOROSUBSTITUTED BENZENE DERIVATIVES IN F-NMR IMAGING

BACKGROUND OF THE INVENTION

The invention relates to new benzene derivatives containing at least two fluorine atoms, their use as NMR diagnostic agents, diagnostic agents that contain these benzene derivatives as well as a process for the production of these compounds and agents.

Modern medical technique makes it possible to represent the smallest morphological structures with a resolution that comes close to that of tissue sections from anatomy textbooks.

However, it is not possible even with the help of ultrasound, X-ray diagnosis, nuclear medicine and even nuclear spin tomography to obtain data on the metabolic physiological condition of a tissue of the living organism. But for a more accurate diagnosis and especially for planning and monitoring of a therapy this knowledge is of considerable importance since an optimal therapy can best be devised when early indications of its effects are possible.

An important parameter of the metabolic physiological activity is the pH. Many pathological processes result in a change of the hydrogen ion concentration. One of the best known examples is the release of lactic acid as a result of inadequate oxygen supply and the anaerobic metabolism of glucose it causes. Anaerobic glycolysis practically always occurs where a sufficient supply of oxygen is no longer guaranteed. A short-term acidification can be detected, for example, in areas of highest muscular activity. But here the accumulating lactic acid is carried away relatively quickly in the resting pause, so that no overacidifying can be detected in the resting muscle. But this appears to be different in areas of permanent oxygen debt. In ischemic areas (infarct) there is a shift of the pH because of the increased anaerobic glycolysis. Similar effects can be observed in rapidly growing neoplasms. Besides a disturbance of regulation, a lack of oxygen is present in the area of a tumor, so that here also an acidification occurs by anaerobic metabolism of carbohydrates.

The determination of the tissue pH thus leads to important statements on the function, condition and growth of cells, so that it is generally desirable to localize metabolic acidosis. (Am. J. Physiol. 246, R 409, 1984; R. Nuccitelli, D. W. Deamer, Eds. 1982 Intracellular pH: Its Measurement, Regulation and Utilization in Cellular Functions, Liss, New York.) Besides the measurement of the pH with pH electrodes, recently NMR spectroscopy has been used for this purpose. With its help, it was possible for the first time to determine the pH of the tissue noninvasively.

Determination of the pH with the help of NMR spectroscopy is based on the measurement of the signals of a chemical compound, which is in a pH-dependent, reversible equilibrium. If this equilibrium is slow relative to the NMR time scale, the signals of all components can be obtained and the signal intensities correspond to the concentrations of the equilibrium components. On the other hand, in the case of a rapid equilibrium, only one signal can be measured and the chemical shift is given by the chemical shift of the equilibrium components and their concentration.

In a two-component equilibrium, with the knowledge of the $pK_a$ and the chemical shift of the components, the pH can be calculated with the help of the Henderson-Hasselbalch equation.

It can be seen from the following table which atomic nuclei in principle are suitable for NMR imaging or spectroscopy:

| No. | Nucleus | Frequency at 1 tesla MHz | Relative Measurement Sensitivity $^1H = 1$ | Concentration in biological tissue | Chemical Shift | Chemical Modification Possibility | $T_1$ Relaxation times (seconds) |
|---|---|---|---|---|---|---|---|
| 1 | $^1H$ | 42.6 | 1.0 | 100 mol/l | small | very high | 0.1-3 |
| 2 | $^{19}F$ | 40.1 | 0.8 | <<1 mmol/l | very great | very high | 1-5 |
| 3 | $^{23}Na$ | 11.3 | 0.09 | 100 mmol/l | ./. | practically zero | <0.1 |
| 4 | $^{31}P$ | 17.2 | 0.06 | 10 mmol/l | average | limited | 1-5 |
| 5 | $^{13}C$ | 10.7 | 0.0002 | 1 mmol/l | very great | very high | 1-10 |

For 15 years the $^{31}P$ nucleus has been used as a noninvasive measuring probe for intracellular pH measurement (J. Biol. Chem. 248, 7276, 1973). In this case the pH-sensitive signal is the signal of the inorganic phosphate from the hydrogen phosphate-dihydrogen phosphate equilibrium; the $^{31}P$ signal of the phosphorus creatine serves as reference.

But the use of the $^{31}P$ nucleus for pH determination also has its limits: thus an exact determination of the pH in a well-localized tissue volume in humans even with the use of 2 T nuclear spin tomographs is not possible. This is due to the relatively low phosphate concentrations as well as the fact that the $^{31}P$ signal metrologically is difficult to register. Interfering signals in the area of the inorganic phosphate, superposition of the inorganic signal by other P metabolites or the lack of a reference signal can prevent a pH measurement. Other difficulties are in the slight sensitivity of the nucleus and the slight pH dependence of the chemical shift. The accuracy of the pH measurement is influenced above all by the determination of the chemical shifts of the signals and is no better than 0.2 pH units. Further, resonance signals can be entirely lacking in case of use of endogenous phosphates, since the compounds accumulate in such small concentrations (e.g., in intestines or in Ehrlich ascites tumor cells), that a pH determination is not possible.

Because of these circumstances only a quite inaccurate pH determination in comparatively large volumes is possible. Signals are picked up in an accumulation time of 15 minutes from a measuring volume of about 100 cc to provide a satisfactory $^{31}P$ spectrum.

In case of use of a nucleus other than $^{31}P$ the $^{19}$fluorine nucleus is the nucleus of choice, since it provides an easily measurable NMR signal, which is very similar to that of the hydrogen proton (it also has a nuclear spin of ½ like $^1H$), i.e., the same receiving and transmitting coils as in $^1H$ NMR diagnosis can be used, it has a great sensitivity (about 83% of $^1H$), is available in 100% frequency and the signals are distributed over a great frequency range. Other advantages to be listed are the absence of fluorine in the organism (except for the teeth), so that no complications with endogenous F signals can occur (lack of a 19F background signal) as well as favorable chemical accessibility.

Data which can be obtained by the use of F molecules in NMR diagnosis cannot be obtained by any other diagnostic imaging or quasi-imaging process: The signal can greatly change in the body—depending on the chemical condition—thus allowing the quantification of biochemical reactions and making possible a direct observation of physiological processes. Despite these tempting properties, there is a problematic concentration consideration. A meaningful experiment requires $^{19}F$ concentrations of greater than 1 mmol of F/l, i.e., the compounds to be applied must exhibit an outstanding tolerability and have a good solubility in water in order that in solutions of high concentration, the smallest possible volumes can be used.

The frequency (chemical shift) of a fluorine line is determined by the position of the F atom in the molecule. In principle, this also applies to all other atomic nuclei, but in the case of the fluorine atom the chemical shift is particularly strongly pronounced. A reference line is required to observe or quantify a shift of the fluorine signal. This frequency line can be the $^1H$ signal, an external F standard or an unchanging F line, which is also located in the area to be measured. This reference line can be located in another, similarly distributing molecule or preferably in the molecule used as indicator. The most favorable situation is in the last-named case, since here only one substance is applied and no problems whatsoever with susceptibility effects occur so that an unequivocal assignment of the signals is possible.

Therefore, there is a need to find suitable compounds which react to a change of the pH with a changed measuring magnitude (resonance frequency) in the NMR spectrum with simultaneous presence of a reference line. Further, these compounds or diagnostic agents containing these compounds must exhibit the following properties:

(a) a great chemical shift per pH unit;
(b) suitable pK values for in vivo measurements;
(c) pharmacokinetics suitable for diagnosis;
(d) a high accumulation in the target organs sufficient for a measurement;
(e) good compatibility and low toxicity;
(f) metabolic stability;
(g) great chemical stability and shelf life; and
(h) good water solubility.

The compounds described so far (and only for in vitro examinations) (Annals of the New York Academy of Science, S. M. Cohen, Ed. 1987, 508, 33) do not meet these requirements. Thus, with them, e.g., a pH determination more accurate than with $^{31}P$ is not possible, since the pH dependence of the chemical shift is too small (smaller than or equal to 1 ppm/pH) and/or their pH values are outside the physiological range and/or their resonance frequencies are dependent not only on the pH but also on the field strength. Also the described compounds, because of their poor compatibility, are not suitable for an animal experiment or not at all for clinical use.

BRIEF DESCRIPTION OF THE DRAWINGS

Various other objects, features, and attendant advantages of the present invention will be more fully appreciated as the same becomes better understood when considered in conjunction with the accompanying drawings, and wherein:

FIG. 1 is the in vivo $^{19}F$ spectrum of a whole rat 5 minutes after administration of 0.5 mmol/kg of 5-[N-(4-fluoro-2-trifluoromethylphenyl)sulfamoyl]isophthalic acid. Measuring time: 4 minutes.

FIG. 2 is the in vivo $^{19}F$ spectrum of the rat 50 minutes after administration of the fluorine compound.

FIG. 3 is the in vivo $^{19}F$ spectrum of the bladder area of a rat 70 minutes after application of the fluorine compound. Measuring time: 20 minutes.

SUMMARY OF THE INVENTION

Figure 1:
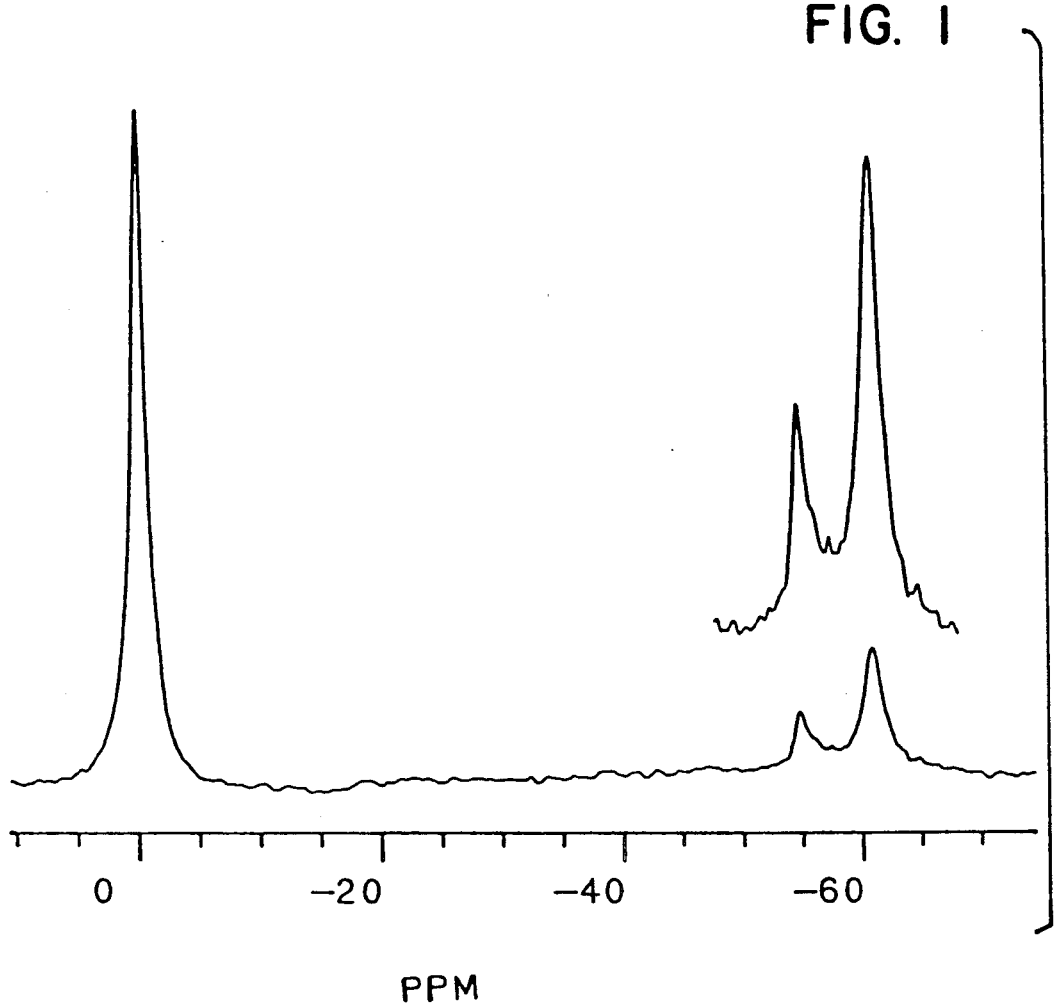
FIGS. 1-3 relate to the experiments described in Example 49.

This invention makes available compounds and agents which exhibit these useful properties, as well as processes for their production.

It has been found that fluorosubstituted benzene derivatives of Formula I

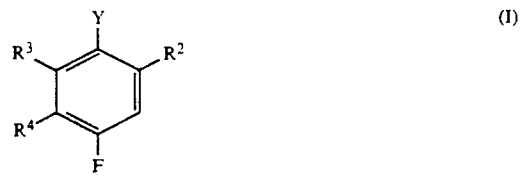

in which

Y represents an OH or $-NHSO_2R^1$ group with $R^1$ meaning a

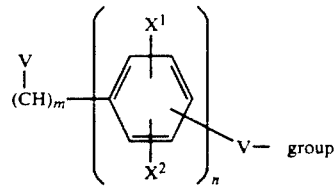

or a straight-chain or branched-chain alkylene group with 1 to 10 carbon atoms, which optionally is substituted by 1 to 6 fluorine atoms and carries a fluorine atom or the radical $-V$ on the end, in which each V independently stands for hydrogen or the radicals $-U-OR^5$ or

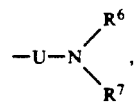

and

U represents a CO or $SO_2$ radical $R^5$ represents hydrogen or a saturated, unsaturated, straight-chain or branched-chain or cyclic hydrocarbon radical, e.g., alkyl, with up to 16 carbon atoms, optionally substituted by 1 to 6 hydroxy groups, $R^6$ and $R^7$, each independently of one another, represent hydrogen, a straight-chain or branched-chain hydrocarbon group, e.g., alkyl, with 1 to 16 carbon atoms, optionally substituted by 1 to 6 hydroxy groups or 1 to 12 fluorine atoms, or $R^6$ and $R^7$ together with the nitrogen atom represent a saturated five- or six-membered heterocyclic ring optionally containing another heteroatom, $X^1$ and $X^2$ independently stand for fluorine, the radical V, a straight-chain or branched-chain alkylene group with 1 to 10 carbon atoms, which optionally is substituted by 1 to 6 fluorine atoms and carries a fluorine atom or the radical V on the end, or the radical $-N(R^6)-CO-R^8$, in which $R^8$ means a straight-chain or branched-chain hydrocarbon, e.g., alkyl, radical with 1 to 16 carbon atoms, which optionally is substituted by 1 to 6 hydroxy groups and 1 to 12 fluorine atoms and optionally is interrupted by 1 to 3 oxygen atoms, m stands for the numbers 0, 1, 2, 3 or 4, n stands for the numbers 0 or 1, and n and m are not both to mean 0 at the same time, $R^2$ means hydrogen, fluorine, the radical $-N(R^6)-CO-R^8$, a

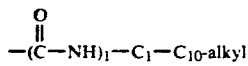

group, which is straight-chain or branched-chain and optionally is substituted with 1 to 6 fluorine atoms, and l stands for the numbers 0 or 1, or a radical

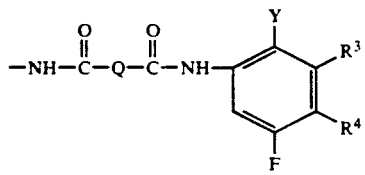

in which Q stands for a $(CF_2)_k$ or $C_6F_4$ group with k meaning the numbers 1, 2, 3, 4, 5 or 6, $R^3$ and $R^4$, each independently of one another, mean hydrogen, fluorine, a straight-chain or branched-chain alkyl group with 1 to 10 carbon atoms, which optionally is substituted by 1 to 6 fluorine atoms, the radical V or $-N(R^6)-CO-R^8$, provided that at least two fluorine atoms are present in the molecule, radicals V present in the molecule can be the same or different, and optionally free acid groups are made into salts with organic or inorganic bases, in a surprising way are outstanding suitable for the production of NMR diagnostic agents.

If $R^1$ and $X^1$, $X^2$ or $R^2$, $R^3$ and $R^4$ stand for an alkylene or alkyl group, this group can be straight-chain or branched-chain, having up to 10 carbon atoms and optionally be substituted by 1 to 6 fluorine atoms. Preferred are alkylene or alkyl substituents with 1 to 6 carbon atoms, which optionally are substituted by 1 to 6 fluorine atoms. As examples there can be mentioned methylene, difluromethylene, ethylene, methylethylene, ethylethylene, trimethylene, tetramethylene, pentamethylene, hexamethylene, 1,1-difluoroethylene, 1-fluorethylene, 1-methyltetramethylene, 1-methyltrimethylene, 2-methyltrimethylene, 2-methyltetramethylene, trifluoromethylmethylene, 2,2-difluoroethylene or in case of $R^2$, $R^3$ and $R^3$ the corresponding alkyl radicals, supplemented by a hydrogen or fluorine atom, such as, for example, methyl, fluoromethyl, trifluoromethyl, ethyl, 2-fluoroethyl, 2,2,2-trifluoroethyl, 1-methylethyl, 1-fluoromethylethyl, 2-fluoro-1-methylethyl, etc.

Suitable as substituents $R^5$, $R^6$, $R^7$ and $R^8$ are saturated, unsaturated, straight-chain or branched-chain or cyclic, preferably saturated hydrocarbon radicals with up to 16 carbon atoms, which optionally are substituted by 1 to 6 hydroxy groups as well as in the case of $R^6$, $R^7$ and $R^8$ by 1 to 12 fluorine atoms.

As examples there can be mentioned the methyl, ethyl, hydroxymethyl, 1-hydroxyethyl, 2-hydroxyethyl, 2-hydroxy-1-(hydroxymethyl)ethyl), 1-(hydroxymethyl)ethyl, propyl, isopropyl, isopropenyl, 2- and 3-hydroxypropyl, 2,3-dihydroxypropyl, butyl, isobutyl, isobutenyl, 2-, 3- and 4-hydroxybutyl, 2-, 3- and 4-hydroxy-2-methylbutyl, 2- and 3-hydroxy-isobutyl, 2,3,4-trihydroxybutyl, cyclohexyl, pentyl, hexyl, bis- and tris(hydroxymethyl)methyl, 2,3-dihydroxy-1-(hydroxymethyl)propyl, 2,3,4,5,6-pentahydroxyhexyl, 1,3,4-trihydroxybutyl-2, as well as 2,2,2-trifluoroethyl, trifluoromethyl, 2-fluoroethyl, 1-fluoromethylethyl group.

Preferred are hydrocarbon radicals with up to 6 carbon atoms and optionally 1 to 5 hydroxy groups as well as 1 to 8 fluorine atoms.

In the case of $R^8$, the alkyl radical can be interrupted by 1 to 3 oxygen atoms. As examples for links contained in $R^8$ there can be listed:

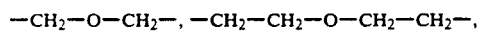

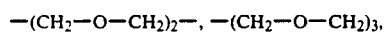

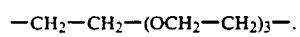

If $R^6$ and $R^7$ together with the nitrogen atom represent a saturated five- or six-membered heterocyclic ring optionally containing another heteroatom, for example, N, O, or S, preferably

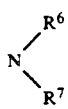

stands for pyrrolidine, piperidine, morpholine or piperazine.

The acid hydrogen atoms present in the compounds of the general formula optionally can be replaced totally or partially by cations of inorganic and/or organic bases or amino acids. Suitable inorganic cations are, for example, the lithium ion, the potassium ion, the calcium ion, the magnesium ion and especially the sodium ion. Suitable cations of organic bases are, inter alia, those of primary, secondary or tertiary amines, such as, for example, ethanolamine, diethanolamine, morpholine, glucamine, N,N-dimethylglucamine and especially N-methylglucamine. Suitable cations of amino acids are, for example, those of lysine, arginine and ornithine as well as the amides of otherwise acid or neutral amino acids.

Production of the fluorosubstituted benzene derivatives of Formula I takes place in that, (a) in compounds of Formula II

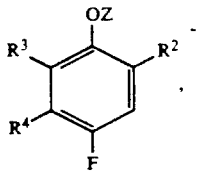

(II)

in which
Z stands for a hydroxy protecting group, protecting group Z is cleaved and optionally protecting groups present in $R^3$ and $R^4$ are removed, or
(b) compounds of Formula III

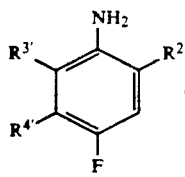

(III)

in which
$R^{3'}$ and $R^{4'}$ stand for $R^3$ and $R^4$ or for radicals to be converted into $R^3$ and $R^4$,
are reacted with compounds Formulae IV or V $$HalSO_2R^{1'}$$ (IV), $$(R^{1'}SO_2)_2)$$ (V), in which
Hal stands for chlorine, bromine, or fluorine, and,
$R^{1'}$, stands for $R^1$ or a radical to be converted into $R^1$, and optionally in the reaction products thus obtained the substituents $R^{1'}$, $R^{3'}$ and $R^{4'}$ are converted into the finally desired substituents $R^1$, $R^3$ and $R^4$ and optionally present free acid groups are made into salts with organic and inorganic bases.

Suitable as protecting group Z are all hydroxyl protecting groups, which are known as suitable for an intermediate hydroxyl group protection, i.e., which are easily introduced and can also be easily cleaved later by re-formation of the finally desired free hydroxyl group. Preferred protecting groups are ether groups such as, e.g., benzyl, di- and tri-phenyl-methyl ether groups as well as acetal and ketal groups with, e.g., acetaldehyde and acetone. The protection by esterification, e.g., by introduction of the benzoyl or acyl, especially the acetyl radical is also often suitable.

Cleavage of protecting groups Z takes place analogously to the process for the protecting groups optionally present in $R^3$ and $R^4$ in a way known in the art, e.g., in the case of a benzyl ether by hydrogenolytic cleavage in the presence of, e.g., palladium carbon, in the case of an ester, e.g., by alkaline saponification in aqueous alcoholic solution at temperatures of 0° to 50° C. or in the case of tert-butyl esters with the help of trifluoroacetic acid, as well as in the case of a ketal cleavage with the help of, e.g., cation exchangers or trifluoroacetic acid.

The synthesis of the desired sulfonamides of Formula I ($Y=NHSO_2R^1$) takes place in a way known in the art (Houben-Weyl, "Methoden der organischen Chemie" [Methods of Organic Chemistry], Vol. IX, pp. 343, 398, 547 and 557, Georg Thieme Verlag Stuttgart 1955) by reaction of amines of Formula III with halosulfonyl derivatives (e.g., chlorosulfonyl ethyl acetate) of Formula IV or sulfonyl anhydrides (e.g., trifluoromethane sulfonic acid anhydride) of Formula V in presence of acid traps such as, e.g., tertiary amine [e.g., triethylamine, pyridine, N,N-dimethylaminopyridine, 1,1-diazabicyclo[4.3.0]nonene-5[DBN], 1,5-diazabicyclo[5.4.0]undecene-5 (DBU), alkali or alkaline-earth carbonate or bicarbonate (e.g., sodium, magnesium, calcium, barium, potassium carbonate and bicarbonate) in solvents such as, e.g., dioxane, dichloroethane, dichloromethane but also in alcohol or water at temperatures between −20° C. and +50° C., preferably −5° to 20° C.

The subsequent reactions optionally to be performed to synthesize the final substances with the desired substituents $R^3$ and $R^4$, such as, e.g., saponification of esters, conversion of a carboxylic acid or sulfuric acid to an amide as well as cleavage of protecting groups follow methods known in the literature. If polyhydroxyalkyl amides are to be produced, it is advantageous to use the polyhydroxyalkyl amines necessary for it in protected form in the reaction, e.g., as O acyl derivatives or as ketals. This applies especially if these derivatives can be produced more easily and cheaply than the polyhydroxyalkyl amines themselves. A typical example is 2-amino-1-(2,2-dimethyl-1,3-dioxolan-4-yl) ethanol, the acetonide of 1-amino-2,3,4-trihydroxybutane, produced according to DE-OS No. 31 50 917.

The subsequent removal of the protecting groups is routine and can take place, e.g., by treatment with an acid ion exchanger in aqueous ethanolic solution.

The educts of Formulae II, III, IV and V necessary for the reactions listed above under (a) and (b) can be purchased or are known in the literature or can be produced analogously to methods known in the literature (e.g., J. Org. Chem. 27, 3134 (1962), J. of Organometallic Chem. 190 [1980], 217, J. Org. Chem. 1984, 49, 2792, JACS 73 [1951], 1325, J. Org. Chem. 1982, 47, 1081, Tet. Lett. 1984, 839).

After production of the desired compound of Formula I, acid hydrogen atoms present in the molecule can be substituted by cations of inorganic and/or organic bases or amino acids.

In this case, neutralization takes place with the help of inorganic bases (for example, hydroxides, carbonates or bicarbonates) from, for example, sodium, potassium, lithium, magnesium and calcium and/or inorganic bases such as, among others, primary, secondary and tertiary amines, such as, for example, ethanolamine, morpholine, glucamine, N-methyl and N,N-dimethylglucamine, as well as basic amino acids, such as, for example, lysine, arginine and ornithine or from amides of originally neutral or acid amino acids.

For the production of neutral salts, an equivalent of the desired bases can be added to the acid benzene derivatives in aqueous solution or suspension. The solution thus obtained can then be evaporated to dryness in a vacuum. Often it is advantageous to precipitate the formed neutral salts by addition of water-miscible solvents such as, for example, lower alcohols (methanol, ethanol, isopropanol and others), lower ketones (acetone and others), polar ethers (tetrahydrofuran, dioxane, 1,2-dimethoxyethane and others) and thus obtain crystallizates that are easy to isolate and purify.

If the acid compounds contain several free acid groups, it is often advisable to produce neutral mixed salts, which contain both inorganic and organic cations as counterions.

Production of the diagnostic agents according to the invention can also take place in a way known in the art by the compounds according to the invention—optionally with addition of the additives usual in galenicals—being suspended or dissolved in aqueous medium and then the suspension or solution being optionally sterilized. Suitable additives are, for example, physiologically safe buffers (such as, for example, trometha- mine), slight additions of complexing agents (such as, for example, diethylenetriaminepentaacetic acid) or, if necessary, electrolytes such as, for example, sodium chloride or, if necessary, antioxidizing agents such as, for example, ascorbic acid.

If for enteral administration or for other purposes, suspensions or solutions of the agents according to the invention in water or physiological salt solution are desired, they are mixed with one or more auxiliary agents usual in galenicals (for example, methylcellulose, lactose, mannitol) and/or surfactant(s) (for example, lecithins, Tweens ® or Myrj ®) and/or aromatic substance(s) for taste correction (for example, essential oils).

The fluorine-containing compounds according to the invention can advantageously be used in, in vivo NMR diagnosis, i.e., for NMR imaging and in NMR spectroscopy as indicator of different parameters. Thus, among others, with the help of the high- sensitivity resolution spectroscopy and thus in a tissue-specific manner, the pH, $pO_2$, $pCO_2$, temperature, redox processes, reaction kinetics can be measured.

Further, it was established that the compounds according to the invention are surprisingly distinguished by a very good tolerability. Thus, for example, an intravenous acute tolerability ($LD_{50}$) of 4 mmol/kg of body weight was determined on the mouse for 5-[N-(4-fluoro-2-trifluoromethylphenyl)sulfamoyl)-isophthalic acid (Example 13). This finding is surprising since most comparable fluorinated compounds exhibit an extremely poor (less than 1 mmol/kg of body weight) tolerability.

The pharmaceutical agents according to the invention are preferably produced in a concentration of 1 micromol-1 mol/1. As a rule they are dosed in amounts of 0.005-20 mmol/kg of body weight, preferably 0.05 to 5 mmol/kg of body weight. They are intended for enteral and parenteral application.

The agents according to the invention meet the varied requirements for suitability as diagnostic agents for NMR tomography and spectroscopy. Further, they exhibit a high efficacy which is necessary to burden the body with the smallest possible amounts of foreign substances, and the good tolerability which is necessary to maintain the noninvasive character of the examinations.

The good water solubility of the agents according to the invention makes it possible to produce highly concentrated solutions, to keep the volume load of the circulatory system within acceptable limits and to balance the dilution by body fluid, i.e., the NMR diagnostic agents must be 100-1000 times more water-soluble than the agents used in in vitro NMR spectroscopy.

The good tolerability of the compounds according to the invention make possible the examination and NMR spectroscopic measurement of the pH in the living organism. In this case, a dose of 10 micromol/kg to 10 mmol/kg of body weight makes possible a determination without problems of the change of the chemical shift of the $^{19}F$ signal relative to the reference signal (e.g., an intramolecular $CF_3$ group) and thus of the pH. The applied solution is quickly distributed in the organism and thus is able to indicate the ranges of different pH. Moreover, by an appropriate dosing a shift of the pH and thus optionally a therapeutic effect can be caused.

To be able to show small changes of the pH, the compounds are advantageous whose pK is close to the biological or pathological pH of the tissue that is of interest. As a rule those compounds are of special interest whose pK is between 2 and 9, preferably between 6 and 8. Compounds which show the pH of the gastrointestinal tract advantageously have a pK between 2 and 8. Since the greatest accuracy of the pH determination is in the range of the greatest change of the chemical shift per unit, i.e., in the pK of the respective compound, a very good analysis of the biological processes is possible. Thus the pH of the blood is about 7.2-7.4; pathological ranges can have a changed pH, which can drop, e.g., to 4.0 or lower.

For the representation of the kidney function or analysis of the primary or secondary urine, compounds with a pK between 5 and 7 are advantageous, since the pH of the urine as a rule is below that of the blood. For the determination of the intragastric pH, compounds are advantageous which most clearly show a change of the chemical shift between pH 2 and 6, since the pH of the gastric juice greatly varies between almost 1 and 7.

By the use of the very easily compatible new type fluorinated measuring probes, it has thus become possible to perform high-sensitivity resolution spectroscopy in smaller volumes (e.g., 10 cc) and to determine physiologically important parameters such as, e.g., the pH accurately in brief measuring time without disturbance or superposition by other molecules.

Said compounds are also suitable for an in vivo imaging (NMR imaging). In this case, not only is the data on the changed chemical shift imaged but also the local concentrations of fluorinated compounds are reproduced by the shooting sequences usual in the MRT in an imaging. The advantage of the $^{19}F$ imaging in comparison with the $^{1}H$ tomography is based on the fact that the distribution of the pharmaceutical agent can be represented directly without superposition by disturbing structures.

There is achieved, e.g., a surprising contrasting of the renal excretory system (kidney, ureter, bladder) after an intravenous dose of the compounds according to the invention, which are applied in a dose of 5 micromol/kg to 20 mmol/kg, preferably of 0.1 mmol/kg to 5 mmol/kg. In this case, it has been surprisingly found that the additional injection of a paramagnetic compound [e.g., GdDTPA (gadolium diethylene triamine pentacetic acid/dimeglumine)] in a dose of 1 micromol/kg to 2 mmol/kg, preferably of 50 micromol/kg to 500 micromol/kg, leads to a marked improvement of the image quality.

The compounds according to the invention, coupled, for example, to suitable monoclonal antibodies, can also be used as organ- and tumor-specific therapeutic agents and diagnostic agents.

The compounds according to the invention of general formula I with Y meaning $NHSO_2R^1$ can also be used against all bacterial infections, which can be treated chemotherapeutically with sulfonamides.

The following examples serve for a more detailed explanation of the object of the invention.

In the foregoing and in the following example, all temperatures are set forth uncorrected in degrees Celsius; and, unless otherwise indicated, all parts and percentages are by weight.

The entire texts of all applications, patents and publications, cited above and below, and of corresponding West German Application No. P 38 34 704.0, filed Oct. 7, 1988, are hereby incorporated by reference.

In the following examples, "Cld" means "calculated", and "Fnd" means "found".

EXAMPLES

Example 1

2-[N (2,4-Difluorophenyl)sulfamoyl]-acetic acid methyl ester 3.87 g (30 mmol) of 2,4-difluoroaniline is dissolved, with exclusion of moisture, in 80 ml of dichloroethane, 2.5 ml (30 mmol) of pyridine is added and the solution is cooled to 0° C. 5.18 g (30 mmol) of chlorosulfonyl ethyl acetate, dissolved in 20 ml of dichloroethane, is instilled in the cooled solution, stirred for 1 hour at 0° C. and 12 hours at room temperature. The reaction solution is then shaken out with 2N hydrochloric acid, the phases are separated, the organic phase is dried on sodium sulfate, concentrated by evaporation in a vacuum and the oily residue is chromatographed on 200 g of silica gel 60 (Merck) with ethyl acetate/hexane. 4.5 g (16.97 mmol) = 56.55% of the theoretical yield of the title compound is obtained as oil.

| Analysis: $C_9H_9F_2NO_4S$ MW 265.24 | | | | | |
|---|---|---|---|---|---|
| Cld: | C 49.75 | H 3.42 | F 14.32 | N 5.28 | O 24.19 S 12.09% |
| Fnd: | 41.03 | 3.61 | 14.11 | 5.13 | 11.91% |

Example 2

2-[N-(2,4-Difluorophenyl)sulfamoyl]-acetic acid 2.68 g (10.1 mmol) of 2-[N-(2,4-difluorophenyl)sulfamoyl]-acetic acid methyl ester is dissolved in 30 ml of dioxane, 15 ml of 2N sodium hydroxide solution is added and stirred for 30 minutes at room temperature. The reaction solution is then evaporated to dryness, the residue is dissolved in some water, the solution is again concentrated by evaporation, the residue is dissolved in 30 ml of water, acidified with 2N hydrochloric acid and the product is extracted with ethyl acetate. The organic phase is dried on sodium sulfate, filtered and evaporated to dryness in a vacuum The crude product is recrystallized from ether/hexane 1:1. 1.55 g (6.17 mmol) = 61.1% of the theoretical yield is obtained as a crystallizate, melting point 110–111.5° C.

Example 3

2 [N (2,4-Difluorophenyl)sulfamoyl]-acetic acid-(2,3,4-trihydroxy butylamide)

(a) 2-[N-(2,4-Difluorophenyl)sulfamoyl)]-acetic acid-[2-hydroxy-2(2,2-dimethyl-1,3-dioxolan-4-yl)-ethylamide]

1.62 g (6.5 mmol) of 2-[N-(2,4-difluorophenylsulfamoyl)]-acetic acid is dissolved in 20 ml of dimethylformamide with exclusion of moisture and under argon atmosphere, 1.01 g (6.5 mmol) of hydroxybenzotriazole and 1.05 g (6.5 mmol) of 2-hydroxy-2-(2,2-dimethyl-1,3-dioxolan-4-yl)-ethylamine are added and the solution is cooled to −10° C. 1.34 g (6.5 mmol) of dicyclohexyl-carbodiimide is added to the cooled solution, it is stirred for 1 more hour at −10° C., the cooling is removed, so that the reaction mixture is slowly warmed to room temperature and stirred for 5 more hours. The suspension is then filtered, the filtrate is evaporated to dryness in a vacuum and the residue is dissolved in ethyl acetate. This solution is shaken out with water, dried on magnesium sulfate, filtered and evaporated to dryness in a vacuum. The residue is dissolved in 50 ml of dichloromethane, the solution is filtered, the filtrate is evaporated to dryness in a vacuum, and the residue is crystallized from diethyl ether. 1.56 g (3.96 mmol) = 60.85% of the theoretical yield is obtained as a crystallizate. Melting point 165–166.5° C.

(b) 2-[N-(2,4-Difluorophenyl)sulfamoyl]-acetic acid-(2,3,4-trihydroxy-butylamide)

2.96 g (7.5 mmol) of 2-[N-(2,4-difluorophenylsulfamoyl)-acetic acid-[2-hydroxy-2-(2,2-dimethyl-1,3-dioxolan-4-yl)-ethyl-amide] is dissolved in 10 ml of methanol, about 100 mg of cation exchanger Amberlyst 15 is added and warmed to boiling temperature in 1 hour. The ion exchanger is then filtered off and the filtrate is evaporated to dryness in a vacuum. 2.21 g (6.26 mmol) = 83.5% of the theoretical yield of the product is obtained as an amorphous solid.

| Analysis: $C_{12}H_{15}F_2N_2O_6S$ MW 353.32 | | | | | |
|---|---|---|---|---|---|
| Cld: | C 40.79 | H 4.27 | F 10.75 | N 7.92 | O 27.16 S 9.07% |
| Fnd: | 41.04 | 4.52 | 10.53 | 8.11 | 8.93% |

Example 4

2-[N-(2,4,6 Trifluorophenyl)sulfamoyl]-acetic acid methyl ester 0.76 g (5 mmol) of 2,4,6-trifluoroaniline is dissolved in 40 ml of dichloroethane with exclusion of moisture, 0.4 ml (5 mmol) of pyridine is added, 0.86 g (5 mmol) of chlorosulfonyl acetic acid methyl ester, dissolved in 10 ml of dichloroethane, is instilled at 0° C. and then it is stirred for 1 hour at 0° C. and 12 hours at room temperature. The reaction solution is then shaken out twice with 10 ml of 2N hydrochloric acid each, the phases are separated, the organic phase is dried on magnesium sulfate, filtered and evaporated to dryness. The residue is crystallized from diethyl ether/pentane 1:1. 790 mg (2.79 mmol) = 55.79% of the theoretical yield is obtained as a crystallizate. Melting point 99–100° C.

Example 5

2-[N-(2,4,6 Trifluorophenyl)sulfamoyl]-acetic acid 1.37 g (4.8 mmol) of 2-[N-(2,4,6-trifluorophenyl)sulfamoyl]-acetic acid methyl ester is dissolved in 15 ml of dioxane, 7.5 ml of 2N sodium hydroxide solution is added and it is stirred for one hour at room temperature. The solution is then evaporated to dryness, the residue is dissolved in water, the solution is acidified with 2N hydrochloric acid and extracted twice with ethyl acetate. The ethyl acetate extract is dried on magnesium sulfate, filtered and evaporated to dryness. The residue is crystallized from diethyl ether. 1.12 g (4.16 mmol) = 86.68% of the theoretical yield is obtained. Melting point 126–127° C.

Example 6

2 [N-(2,4,6-Trifluorophenyl)sulfamoyl]-acetic acid-[2,3,4 trihydroxy-butylamide]

(a) 2-[N-(2,4,6-Trifluorophenyl)sulfamoyl]-acetic acid-[2-hydroxy-2-(2,2-dimethyl-1,3-dioxolan-4-yl)-ethylamide]

1.38 g (3.16 mmol) of 2-[N-(2,4,6-trifluorophenyl)sulfamoyl] acetic acid is dissolved in 20 ml of DMF with exclusion of moisture and under argon atmosphere, 509 mg (3.16 mmol) of 2-hydroxy-2-(2,2-dimethyl-1,3-dioxolan-4-yl)-ethylamine and 484 mg (3.16 mmol) of hydroxybenzotriazole are added and the solution is cooled to $-10°$ C. 652 mg (3.16 mmol) of dicyclohexylcarbodiimide is added to the cooled solution, it is stirred for one hour at $-10°$ C and for 12 more hours at room temperature. The turbid reaction solution is then filtered and the clear filtrate is evaporated to dryness in a vacuum. The residue is dissolved in 100 ml of ethyl acetate and the solution is shaken out five times with saturated sodium bicarbonate solution and twice with water. The ethyl acetate solution is dried on sodium sulfate, filtered and evaporated to dryness. The residue is chromatographed on silica gel 60 (Merck) with ethyl acetate/methylene chloride 8:2. The corresponding fractions together contain 0.62 g (1.42 mmol)=45% of the theoretical yield of product is obtained as an amorphous solid.

| Analysis: $C_{15}H_{19}F_3N_2O_6S$ MW 412.38 | | | | | |
|---|---|---|---|---|---|
| Cld: | C 43.68 | H 4.64 | F 13.82 | N 6.79 | O 23.27 | S 7.77% |
| Fnd: | 43.42 | 4.87 | 13.66 | 7.02 | | 7.53% |

(b) 2-[N-(2,4,6-trifluorophenyl)sulfamoyl]-acetic acid-[2,3,4-trihydroxy-butylamide]

2.22 g (6 mmol) of 2-[N-(2,4,6-trifluorophenyl)sulfamoyl]-acetic acid-[2-hydroxy-2-(2,2-dimethyl-1,3-dioxolan-4-yl)-ethyl-amide] is dissolved in a mixture of 10 ml of methanol and 5 ml of water, about 100 mg of cation exchanger Amberlyst 15 is added and it is warmed to boiling temperature in 1 hour. The ion exchanger is then filtered off and the filtrate is evaporated to dryness in a vacuum. 1.94 g (5.24 mmol) =87.3% of the theoretical yield of the product is obtained as an amorphous solid.

| Analysis: $C_{12}H_{14}F_3N_2O_6S$ MW 371.31 | | | | | |
|---|---|---|---|---|---|
| Cld: | C 38.81 | H 3.8 | F 15.35 | N 7.54 | O 25.85 | S 8.63% |
| Fnd: | 39.04 | 3.96 | 15.13 | 7.73 | | 8.47% |

Example 7

2-[N-(4-Fluoro-2-trifluoromethylphenyl)sulfamoyl]-acetic acid methyl ester 5 g (27.64 mmol) of 4-fluoro-2-(trifluoromethyl)-aniline is dissolved in 25 ml of dry pyridine and the solution is cooled to 0° C. A solution of 4.82 g (27.4 mmol) of chlorosulfonyl acetic acid methyl ester in 20 ml of dichloromethane is instilled in the cooled solution in the course of about 10 minutes with the temperature being maintained. Then it is stirred for 6 hours at room temperature. The reaction solution is then diluted with 100 ml of dichloromethane, the pyridine is shaken out with 2N hydrochloric acid, the organic phase is dried on magnesium sulfate, filtered and evaporated to dryness. The residue is crystallized from diethyl ether/hexane yield is obtained as a crystallizate. Melting point 84°–86° C.

Example 8

2 [N-(4-Fluoro-2 trifluoromethylph-enyl)sulfamoyl]-acetic acid 2.2 g (6.98 mmol) of 2-[N-(4-fluoro-2-trifluoromethylphenyl)sulfamoyl]-acetic acid methyl ester is dissolved in 20 ml of dioxane, and the solution is mixed with 10 ml (20 mmol) of 2N sodium hydroxide solution. A slight warming occurs and the saponification is complete after 10 minutes. The solution is neutralized with 2N hydrochloric acid with pH control and gently evaporated to dryness in a vacuum. The residue is extracted with 30 ml ethyl acetate, the solution is shaken out once with 10 ml of water, the organic phase is dried on magnesium sulfate, filtered and evaporated to dryness. 1.96 g (6.51 mmol)=93.2% of the theoretical yield is obtained. Melting point 120–121° C. (ether/hexane).

| Analysis: $C_9H_7F_4NO_4S$ MW 301.24 | | | | | |
|---|---|---|---|---|---|
| Cld: | C 35.89 | H 2.34 | F 25.23 | N 4.65 | O 21.25 | S 10.64% |
| Fnd: | 36.05 | 2.36 | 25.45 | 4.66 | | 10.79% |

Example 9

2 [N-(4-Fluoro-2-(trifluoromethylphenyl)sulfamoyl]-acetic acid-(2,3,4-trihydroxy-butyl-amide)

(a) 2-[N-(4-Fluoro-2-(trifluoromethylphenyl)sulfamoyl]-acetic acid-[2-hydroxy-2-(2,2-dimethyl-1,3-dioxolan-4-yl)-ethyl-amide]

3.01 g (10 mmol) of 2-[N-(4-fluoro-2-trifluoromethylphenyl)sulfamoyl]-acetic acid is dissolved in 100 ml of dimethylformamide, 1.54 g (10 mmol) of hydroxybenzotriazole and 1.61 g (10 mmol) of 2-hydroxy-2-(2,2-dimethyl-1,3-dioxolan-4-yl)-ethylamine are added and the mixture is cooled to $-10°$ C. Then 2.07 g (10 mmol) of dicyclohexylcarbodiimide is added, stirred for 1 hour at $-10°$ C and 12 hours at room temperature. After addition of 10 mmol of triethylamine it is stirred for 5 more hours. The solution is concentrated by evaporation in a vacuum, the residue is dissolved in methylene chloride, shaken out with water, the organic phase is dried on magnesium sulfate, concentrated by evaporation and the residue is chromatographed on silica gel. 2.76 g=62.11% of the theoretical yield is obtained as an amorphous solid, of which is crystallized from ethyl acetate. Thus, 1.05 g=23.63% of theory of crystallizate is obtained. Melting point 125°–126° C.

(b) 2-[N-(4-Fluoro-2-(trifluoromethylphenyl)sulfamoyl]-acetic acid-(2,3,4-trihydroxy-butyl-amide)

1.5 g (4.05 mmol) of the substance obtained according to 9(a) is dissolved in 68 ml of a mixture of ethanol and water 1:1. 0.1 ml of conc. hydrochloric acid is added and the solution is stirred for 10 minutes at room temperature and 1 hour at 60° C. The ketal cleavage is then complete. The chloride is removed by addition of anion exchanger and it is concentrated by evaporation in a vacuum. 570 mg=41.45% of the theoretical yield is obtained as an amorphous solid.

| Analysis: $C_{13}H_{16}F_4N_2O_6S$ MW 404.45 | | | | | |
|---|---|---|---|---|---|
| Cld: | C 38.61 | H 3.99 | F 18.79 | N 6.93 | O 23.8 | S 7.93% |
| Fnd: | 38.44 | 4.63 | 18.61 | 6.94 | | 8.13% |

Example 10

4-[N-(4-Fluoro-2-trifluoromethylphenyl)sulfamoyl]-benzoic acid 2.21 g (10 mmol) of 4-chlorosulfonyl-benzoic acid is suspended in 30 ml of dichloromethane with exclusion of moisture, the suspension is cooled to $-5°$ C and, at this temperature, a solution of 1.79 g (10 mmol) of 4-fluoro-2-(trifluoromethyl)-aniline and 1 ml of pyridine in 20 ml of dichloromethane is instilled. When the instillation is completed, it is allowed to come to room temperature and is stirred for 12 more hours. The resulting precipitate is suctioned off and extracted with ether. The ether extract and the filtrate are concentrated by evaporation together and the residue is dissolved in dichloroethane. The solution is extracted three times with 10 ml of saturated sodium bicarbonate solution each. The combined aqueous extracts are acidified with 2N hydrochloric acid and the product thus precipitating is filtered off. The filter residue is evaporated to dryness in a vacuum at 50° C. 3.3 g (9.08 mmol)=90.84% of the theoretical yield is obtained.

| Analysis: $C_{14}H_9F_4NO_4S$ MW 363.28 | | | | | |
|---|---|---|---|---|---|
| Cld: | C 46.29 | H 2.5 | F 20.92 | N 3.86 | O 17.62 | S 8.83% |
| Fnd: | 46.10 | 2.67 | 21.16 | 3.84 | | 8.96% |

Example 11

4-[N-(4-Fluoro-2 trifluoromethylphenyl)sulfamoyl]-benzoic acid (2,3,4-trihydroxy butyl-amide)

(a)

4-[N-(4-Fluoro-2-trifluoromethylphenyl)sulfamoyl]-benzoic acid-[2-hydroxy-2-(2,2-dimethyl-1,3-dioxolan-4-yl)-ethyl-amide]

3.63 g (10 mmol) of 4-[N-(4-fluoro-2-trifluoromethylphenyl)sulfamoyl]-benzoic acid is suspended in 36 ml of ethyl acetate, 2.38 g (20 mmol) of thionylchloride is added and the suspension is heated to boiling temperature. After 15 minutes a clear solution is present, after 1 hour the formation of the acid chloride is complete. The solution is evaporated to dryness under reduced pressure, the residue is concentrated by evaporation in a vacuum twice with 50 ml of dichloromethane each and the dissolved in 36 ml of dioxane. 1.21 g (12 mmol) of triethylamine and 1.93 g (12 mmol) of 2-hydroxy-2-(2,2-dimethyl-1,3-dioxolan-4-yl)-ethylamine are added to this solution and it is stirred for 5 hours at room temperature. The reaction solution is then evaporated to dryness in a vacuum, the residue is extracted with ethyl acetate, the ethyl acetate extract is concentrated by evaporation in a vacuum and the residue is chromatographed on silica gel 60 (Merck) with ethyl acetate/hexane. 3.19 g (6.3 mmol) =63% of the theoretical yield of the product is obtained as an amorphous solid.

| Analysis: $C_{21}H_{22}F_4N_2O_6S$ MW 506.47 | | | | | |
|---|---|---|---|---|---|
| Cld: | C 49.8 | H 4.37 | F 15.0 | N 5.53 | O 18.95 | S 6.33% |
| Fnd: | 50.04 | 4.43 | 14.83 | 5.32 | | 6.18% |

(b)

4-[N-(4-Fluoro-2-trifluoromethylphenyl)sulfamoyl]-benzoic acid-(2,3,4-trihydroxy-butyl)-amide 2.53 g (5 mmol) of 4-[N-(4-fluoro-2-trifluoromethylphenyl)sulfamoyl]-benzoic acid-[2-hydroxy-2-(2,2-dimethyl-1,3-dioxolan-4-yl)-ethylamide] is dissolved in 20 ml of methanol/water 1:1, about 100 mg of cation exchanger Amberlyst 15 is added and warmed for 1 hour to boiling temperature. The ion exchanger is then filtered off and the filtrate is evaporated to dryness in a vacuum. 1.74 g (3.75 mmol)=75% of the theoretical yield of the product is obtained as an amorphous solid.

| Analysis: $C_{18}H_{17}F_4N_2O_6S$ MW 465.4 | | | | | |
|---|---|---|---|---|---|
| Cld: | C 46.45 | H 3.68 | F 16.32 | N 6.01 | O 20.62 | S 6.89% |
| Fnd: | 46.33 | 3.87 | 16.16 | 5.89 | | 7.03% |

Example 12

5-[N-(4-Fluoro-2-trifluoromethylphenyl)sulfamoyl]-isophthalic acid-dimethyl ester 5 g (27.64 mmol) of 4-fluoro-2-(trifluoromethyl)-aniline is dissolved in 70 ml of dichloroethane with exclusion of moisture, 4.38 g (55.28 mmol) of pyridine is added and the solution is cooled to 0° C. With this temperature being maintained, a solution of 8.78 g (30 mmol) of 4-chlorosulfonyl-isophthalic acid dimethyl ester in 50 ml of dichloroethane is instilled, is stirred for 30 minutes at 0° C and for 5 more hours at room temperature. The suspension is shaken out three times with 2N hydrochloric acid and twice with water, the organic phase is dried on sodium sulfate, filtered, concentrated by evaporation and the residue is chromatographed on silica gel 60 (Merck) with ethyl acetate/hexane 1:1. The fractions of the corresponding polarity, concentrated by evaporation, yield 8.94 g (20.54 mmol)=74.3% of the theoretical yield is obtained as a crystalline product. Melting point 142°-150° C.

Example 13

5 [N-(4-Fluoro-2 trifluoromethylphenyl)sulfamoyl]-isophthalic acid 7.03 g (16.15 mmol) of 5-[N-(4-fluoro-2-trifluoromethylphenyl)sulfamoyl]-isophthalic acid-dimethyl ester is dissolved in 50 ml of dioxane, 28.27 ml (56.53 mmol) of 2N NaOH is added and stirred for 3 hours at 50° C. The solution is then concentrated by evaporation under reduced pressure to about 20 ml, acidified with 2N hydrochloric acid and the solid precipitate, which thus results, is suctioned off. The filter residue is dissolved in ethyl acetate, the solution is shaken out twice with water, dried on sodium sulfate, filtered and evaporated to dryness The residue is crystallized from ethyl acetate/hexane 1:1. 5.78 g (14.19 mmol)=87.87% of the theoretical yield is obtained as a crystallizate. Melting point 250°-254° C.

Example 14

5-[N (4-Fluoro 2-trifluoromethylphenyl)sulfamoyl]-isophthalic acid-bis(2,3,4-trihydroxy-butyl-amide)

(a)

5-[N-(4-Fluoro-2-trifluoromethylphenyl)sulfamoyl]-isophthalic acid-bis[2-hydroxy-2-(2,2-dimethyl-1,3-dioxolan-4-yl)-ethylamide 4.89 g (12 mmol) of 5-[N-(4-fluoro-2-trifluoromethylphenyl)sulfamoyl]-isophthalic acid is dissolved in 50 ml of dry dimethylformamide under argon atmosphere, 2.76 g (18 mmol) of hydroxybenzotriazole and 2.9 g (18 mmol) of 2-hydroxy-2-(2,2-dimethyl-1,3-dioxolan-4-yl)-ethylamine are added and the solution is cooled to −10° C. At this temperature, 3.71 g (18 mmol) of dicyclohexylcarbodiimide is added to the solution, is stirred for 1 hour at −10° C and 10 hours at room temperature. The turbid reaction solution is filtered and the filtrate is concentrated by evaporation in a vacuum. The residue is dissolved in 100 ml of ethyl acetate, the solution is shaken out five times with saturated sodium bicarbonate solution and twice with water, the organic phase is dried on sodium sulfate, filtered and concentrated by evaporation. The residue is crystallized from ethyl acetate/hexane 1:1. 3.85 g (5.55 mmol)=46.25% of the theoretical yield is obtained as a crystallizate. Melting point 75°–80° C.

| Analysis: $C_{29}H_{35}F_4N_3O_{10}S$ MW 693.67 |       |       |       |       |        |
|------|-------|-------|-------|-------|--------|
| Cld: | C 50.21 | H 5.09 | F 10.95 | N 6.06 | O 23.06 | S 4.62% |
| Fnd: | 50.35 | 5.16 | 10.67 | 6.09 | | 4.4% |

(b)

5-[N-(4-Fluoro-2-trifluoromethylphenyl)sulfamoyl]-isophthalic acid-bis(2,3,4-trihydroxybutyl-amide)

3.79 g (5.46 mmol) of 5-[N-(4-fluoro-2-trifluoromethylphenyl)sulfamoyl]-isophthalic acid-bis[2-hydroxy-2-(2,2-dimethyl-1,3-dioxolan-4-yl)-ethylamide] is dissolved in a mixture of 40 ml of ethanol and 10 ml of water and the solution is acidified with dilute hydrochloric acid to pH 1. It is stirred at this pH for 4 hours at 60° C. The solution is then adjusted to pH 6.1 with the anion exchanger Amberlite IRA 67, filtered and evaporated to dryness in a vacuum. The solid amorphous residue is dried in a vacuum at 50° C. 2.55 g (4.16 mmol) =76.12% of the theoretical yield is obtained as an amorphous solid.

| Analysis: $C_{23}H_{27}F_4N_3O_{10}S$ MW 613.54 |       |       |       |       |        |
|------|-------|-------|-------|-------|--------|
| Cld: | C 45.03 | H 4.44 | F 12.39 | N 6.85 | O 26.08 | S 5.23% |
| Fnd: | 45.28 | 4.67 | 12.12 | 6.68 | | 4.9% |

Example 15

3 [N-(4-Fluoro-2-trifluoromethylphenyl)sulfamoyl]-benzoic acid 2.21 g (10 mmol) of 3-chlorosulfonyl-benzoic acid is suspended in 30 ml of dichloromethane with exclusion of moisture, the suspension is cooled to −5° C. and, at this temperature, a solution of 1.79 g (10 mmol) of 4-fluoro- 2-(trifluoromethyl)-aniline and 1 ml of pyridine in 20 ml of dichloromethane is instilled. After the instillation is completed, it is allowed to come to room temperature and stirred for 12 more hours. The resulting precipitate is suctioned off and extracted with ether. This ether extract and the filtrate are concentrated by evaporation together and the residue dissolved in dichloroethane. The solution is extracted three times with 10 ml of saturated sodium bicarbonate solution each. The combined aqueous extracts was acidified with 2N hydrochloric acid and the product, thus precipitating, is filtered off. The filter residue is dried in a vacuum at 50° C. 3.04 g (8.37 mmol)=83.7% of the theoretical yield is obtained.

| Analysis: $C_{14}H_9F_4NO_4S$ MW 363.28 |       |       |       |       |        |
|------|-------|-------|-------|-------|--------|
| Cld: | C 46.22 | H 2.5 | F 20.92 | N 3.86 | O 17.62 | S 8.96% |
| Fnd: | 45.97 | 2.68 | 21.14 | 4.02 | | 8.67% |

Example 16

3-[N-(4-Fluoro-2-trifluoromethylphenyl)sulfamoyl]-benzoic acid-[2,3,4-trihydroxy-butyl)-amide]

(a)

3-[N-(4-Fluoro-2-trifluoromethylphenyl)sulfamoyl]-benzoic acid-[2-hydroxy-2-(2,2-dimethyl-1,3-dioxolan-4-yl)-ethylamide]

3.63 g (10 mmol) of 3-[N-(4-fluoro-2-trifluoromethylphenyl)sulfamoyl]-benzoic acid is suspended in 36 ml of ethyl acetate, 2.38 g (20 mmol) of thionylchloride is added and the suspension is heated to boiling temperature. After 15 minutes, a clear solution is present, after 1 hour the formation of the acid chloride is complete. The solution is evaporated to dryness under reduce pressure, the residue is concentrated by evaporation in a vacuum twice with 50 ml of dichloromethane each and then dissolved in 36 ml of dioxane. 1.21 g (12 mmol) of triethylamine and 1.93 g (12 mmol) of 2-hydroxy-2-(2,2-dimethyl-1,3-dioxolan-4-yl)-ethylamine are added to this solution and it is stirred for 5 hours at room temperature. The reaction mixture is then evaporated to dryness in a vacuum, the residue is extracted with ethyl acetate, the ethyl acetate extract is concentrated by evaporation in a vacuum and the residue is chromatographed on silica gel 60 (Merck) with ethyl acetate/hexane. 3.42 g (6.75 mmol) =67.5% of the theoretical yield of the product is obtained as an amorphous solid.

| Analysis: $C_{21}H_{22}F_4N_2O_6S$ MW 506.47 |       |       |       |       |        |
|------|-------|-------|-------|-------|--------|
| Cld: | C 49.8 | H 4.37 | F 15.0 | N 5.53 | O 18.95 | S 6.33% |
| Fnd: | 50.04 | 4.53 | 14.86 | 5.77 | | 6.17% |

(b)

3-[N-(4-Fluoro-2-trifluoromethylphenyl)sulfamoyl]-benzoic acid-[2,3,4-trihydroxy-butyl)-amide]

2.53 g (5 mmol) of 3-[N-(4-fluoro-2-trifluoromethylphenyl)sulfamoyl]-benzoic acid-[2-hydroxy-2-(2,2-dimethyl-1,3-dioxolan-4-yl)-ethylamide] is dissolved in 20 ml of methanol/water 1:1, about 100 mg of cation exchanger Amberlyst 15 is added and warmed to boiling temperature in 1 hour. The ion exchanger is then filtered off and the filtrate is evaporated to dryness in a vacuum. 1.94 g (4.18 mmol)=83.5% of the theoretical yield of the product is obtained as an amorphous solid.

| Analysis: $C_{18}H_{17}F_4N_2O_6S$ MW 465.4 | | | | | | |
|---|---|---|---|---|---|---|
| Cld: | C 46.45 | H 3.68 | F 16.32 | N 6.01 | O 20.62 | S 6.89% |
| Fnd: | 46.63 | 3.92 | 16.11 | 5.87 | | 6.72% |

Example 17

3-[N-(4-Fluoro-2-trifluoromethylphenyl)sulfamoyl]-benzenesulfonic acid-(2,3,4-trihydroxy-butyl)-N-methyl-amide (a)
3-[N-(4-Fluoro-2-trifluoromethylphenyl)sulfamoyl]-benzenesulfonic acid chloride 8.78 g (30 mmol) of 4-fluoro-2-(trifluoromethyl)-aniline is dissolved in 88 ml of dichloroethane with exclusion of moisture, 5.55 g (70 mmol) of pyridine is added and the solution is cooled to 0° C. With this temperature being maintained, a solution of 9.9 g (36 mmol) of 1,3-benzenedisulfonic acid dichloride in 50 ml of dichloroethane is instilled, it is stirred for 30 more minutes at 0° C. and for 5 hours more at room temperature. The suspension is shaken out three times with 2N hydrochloric acid and twice with water, the organic phase is dried on sodium sulfate, filtered, concentrated by evaporation and the residue is chromatographed on silica gel 60 (Merck) with ethyl acetate/hexane 1:1. The fractions of the corresponding polarity, concentrated by evaporation, yield 9.7 g (23.22 mmol)=77.4% of the theoretical yield is obtained of a partially crystalline product.

| Analysis: $C_{13}H_8ClF_4NO_4S_2$ MW 417.78 | | | | | | | |
|---|---|---|---|---|---|---|---|
| Cld: | C 37.37 | H 1.93 | Cl 8.48 | F 18.19 | N 3.35 | O 15.31 | S 15.35% |
| Fnd: | C 37.54 | H 2.12 | Cl 8.22 | F 17.96 | N 3.55 | | S 15.16% |

(b)
3-[N-(4-Fluoro-2-trifluoromethylphenyl)sulfamoyl]-benzenesulfonic acid-[2-hydroxy-2-(2,2-dimethyl-1,3-dioxolan-4-yl)-N-methylethylamide]

8.36 g (20 mmol) of 3-[N-(4-fluoro-2-trifluoromethylphenyl)sulfamoyl]-benzenesulfonic acid chloride is dissolved in 40 ml of tetrahydrofuran, 2.52 g (25 mmol) of triethylamine and 4.03 (25 mmol) of 2-hydroxy-2-(2,2-dimethyl-1,3-dioxolan-4-yl)-N-methylethylamine are added and stirred for 3 hours at 45° C. The reaction mixture is then concentrated by evaporation under reduced pressure, the residue is extracted with ethyl acetate and the extract is chromatographed on silica gel 60 (Merck) with ethyl acetate/hexane. 9.35 g (16.8 mmol)=84% of the theoretical yield is obtained as an amorphous solid.

| Analysis: $C_{21}H_{24}F_4N_2O_7S_2$ MW 556.55 | | | | | | |
|---|---|---|---|---|---|---|
| Cld: | C 45.32 | H 4.34 | F 13.65 | N 5.03 | O 20.12 | S 11.52% |
| Fnd: | 45.57 | 4.61 | 13.37 | 5.22 | | 11.71% |

(c) 3-[N-(4-Fluoro-2-trifluoromethylphenyl)sulfamoyl]-benzenesulfonic acid-(2,3,4-trihydroxybutyl)amide 2.78 g (5 mmol) of 3-[N-(4-fluoro-2-trifluoromethylphenyl)sulfamoyl]-benzenesulfonic acid-[2-hydroxy-2-(2,2-dimethyl-1,3-dioxolan-4-yl)-ethylamide] is dissolved in 10 ml of methanol, 10 ml of water and a catalytic amount of cation exchanger Amberlyst 15 are added and boiled for 1 hour. The ion exchanger is filtered off and the filtrate is evaporated to dryness. 2.12 g (4.12 mmol)=82.3% of the theoretical yield of the product is obtained as an amorphous solid.

| Analysis: $C_{18}H_{19}F_4N_2O_7S_2$ | | | | | MW 515.48 | |
|---|---|---|---|---|---|---|
| Cld: | C 41.94 | H 3.71 | F 14.74 | N 5.43 | O 21.72 | S 12.44% |
| Fnd: | 41.7 | 3.96 | 14.55 | 5.32 | | 12.57% |

Example 18

4-[N (4-Fluoro-2-trifluoromethyl-phenyl)sulfamoylmethyl]-benzoic acid methyl ester 5.29 g (29.5 mmol) of 4-fluoro-2-trifluoromethyl)-aniline and 5 ml of pyridine are dissolved in 200 ml of dichloromethane with exclusion of moisture and the solution is cooled to 0° C. 7.5 g (29.5 mmol) of 4-chlorosulfonylmethylbenzoic acid methyl ester is added to this solution by portions and stirred for 1 hour at 0° C. The reaction mixture is washed pyridine-free with 2N hydrochloric acid, shaken out twice with water, the organic phase is dried on sodium sulfate, filtered and evaporated to dryness. The residue is dried in a vacuum. 10.27 g (26.24 mmol)=89% of the theoretical yield is obtained.

| Analysis: $C_{16}H_{13}F_4NO_4S$ | | | | | MW 391.34 | |
|---|---|---|---|---|---|---|
| Cld: | C 49.11 | H 3.35 | F 19.42 | N 3.58 | O 16.35 | S 8.19% |
| Fnd: | 49.39 | 3.23 | 19.67 | 3.66 | | 8.15% |

Example 19

4-[N-(4 Fluoro-2-trifluoromethylphenyl)sulfamoylmethyl]-benzoic acid 8.6 g (21.98 mmol) of 4-[N-(4-fluoro-6-trifluoromethylphenyl)sulfamoylmethyl]benzoic acid methyl ester is dissolved or suspended in 150 ml of dioxane, 25 ml (50 mmol) of 2N sodium hydroxide solution is added and stirred for 15 minutes at 60° C. The solution is then acidified with concentrated hydrochloric acid, and the acid precipitates out as solid. It is suctioned off, washed with water and dissolved in 50 ml of ethyl acetate. The solution is dried on sodium sulfate, filtered, concentrated by evaporation and the residue is dried in a vacuum. 7.35 g (19.48 mmol)=88.62% of the theoretical yield is obtained.

| Analysis: $C_{15}H_{11}F_4NO_4S$ | | | | | MW 377.31 | |
|---|---|---|---|---|---|---|
| Cld: | C 47.75 | H 2.94 | F 20.14 | N 3.71 | O 16.96 | S 8.5% |
| Fnd: | 47.88 | 3.07 | 20.25 | 3.56 | | 8.35% |

Example 20

4-[N-(4-Fluoro-2-trifluoromethylphenyl)sulfamoylmethyl]-benzoic acid-(2,3,4-trihydroxy-butyl)amide (a) 4-[N-(4-Fluoro-2-trifluoromethylphenyl)sulfamoylmethyl]-benzoic acid-[2-hydroxy-2-(2,2-dimethyl-1,3-dioxolan-4-yl)-ethylamide]

3.24 g (8.59 mmol) of 4-[N-(4-Fluoro-2-trifluoromethylphenyl)sulfamoylmethyl]-benzoic acid is dissolved in 30 ml of DMF with exclusion of moisture, 1.32 g (8.59 mmol) of hydroxybenzotriazole and 1.39 g (8.59 mmol) of 2-hydroxy-2-(2,2-dimethyl-1,3-dioxolan-4-yl)-ethylamine are added and the solution is cooled to −10° C. 1.77 g (8.59 mmol) of dicyclohexylcarbodiimide is added by portions to the cooled solution, it is stirred for 1 more hour at −10° C and for 5 hours more at room temperature. The precipitate of the dicyclohexylurea is then suctioned off, the filtrate is concentrated by evaporation in a vacuum. The residue is dissolved in 100 ml of ethyl acetate, the solution is shaken out with saturated bicarbonate solution and with water, dried on sodium sulfate, filtered and evaporated to dryness. The residue is dried in a vacuum. 3.99 g (7.67 mmol)=89.24% of the theoretical yield is obtained.

| Analysis: $C_{22}H_{24}F_4N_2O_6S$ | | | | | MW 520.5 |
|---|---|---|---|---|---|
| Cld: C 50.77 | H 4.65 | F 14.6 | N 5.38 | O 18.44 | S 6.16% |
| Fnd: 50.94 | 4.71 | 14.42 | 5.42 | | 6.14% |

(b) 4-[N-(4-Fluoro-2-trifluoromethylphenyl)sulfamoylmethyl]-benzoic acid-(2,3,4-trihydroxybutyl)amide 2.6 g (5 mmol) of 4-[N-(4-fluoro-2-trifluoromethylphenyl)sulfamoylmethyl]-benzoic acid-[2-hydroxy-2-(2,2-dimethyl-1,3-dioxolan-4-yl)-ethylamide] is suspended in 20 ml of water/ethanol 1:1, acidified to pH 1 with hydrochloric acid and stirred for 1 hour at 60° C. The reaction solution is neutralized with anion exchanger Amberlite IRA 67, the ion exchanger is filtered off and the filtrate evaporated to dryness in a vacuum. The residue is dried in a vacuum. 2.2 g (4.58 mmol)=91.58% of the theoretical yield is obtained.

| Analysis: $C_{19}H_{20}F_4N_2O_6S$ | | | | | MW 480.43 |
|---|---|---|---|---|---|
| Cld: C 47.5 | H 4.2 | F 15.82 | N 5.83 | O 19.98 | S 6.67% |
| Fnd: 47.55 | 4.4 | 15.65 | 5.91 | | 6.73% |

Example 21

2 Fluoro-5 trifluoromethylsulfamoyl-benzoic acid (a) 2-Fluoro-5-(trifluoromethylsulfamoyl)-benzoic acid methyl ester 3.83 g (20 mmol) of 5-amino-2-fluoro-benzoic acid hydrochloride is dissolved in 30 ml of dioxane, 3.56 g (45 mmol) of pyridine is added, the solution is cooled to 5° C. and, with this temperature being maintained and with exclusion of moisture a solution of 8.46 g (30 mmol) of trifluoromethanesulfonic acid anhydride in 30 ml of dioxane is instilled. It is stirred for 2 more hours at 5° C. and for 2 hours more at room temperature, the reaction solution is concentrated by evaporation with reduced pressure and the residue is dissolved in 100 ml of methanol. This solution is mixed with 1 ml of concentrated sulfuric acid and then is boiled for 3 hours. The methanol is then mostly distilled off in a vacuum, the concentrate is dissolved in 100 ml of dichloroethane and shaken out three times with 30 ml of water each. The organic phase is dried on sodium sulfate, concentrated by evaporation and the residue is chromatographed on silica gel 60 (Merck) with ethyl acetate/hexane. 3.97 g (13.18 mmol)=65.9% of the theoretical yield is obtained of a predominantly crystalline product.

| Analysis: $C_9H_7F_4NO_4S$ | | | | | MW 301.22 |
|---|---|---|---|---|---|
| Cld: C 35.88 | H 2.34 | F 25.22 | N 4.65 | O 21.24 | S 10.64% |
| Fnd: 36.03 | 2.55 | 24.97 | 4.53 | | 10.47% |

(b) 2-Fluoro-5-trifluoromethylsulfamoyl)-benzoic acid 3 g (10 mmol) of 2-fluoro-5-trifluoromethylsulfamoyl)-benzoic acid methyl ester is dissolved in 30 ml of dioxane, 7.5 ml (15 mmol) of 2N sodium hydroxide solution is added and it is stirred for hour at 50° C. The solution is then concentrated by evaporation in a vacuum, the residue is dissolved in 30 ml of water and the solution is acidified with concentrated hydrochloric acid. The acid aqueous solution is extracted with ethyl acetate. The ethyl acetate extract is dried on sodium sulfate, filtered and concentrated by evaporation. The residue is crystallized from ethyl acetate. 2.12 g (7.38 mmol) of the theoretical yield is obtained as a crystallizate.

| Analysis: $C_8H_5F_4NO_4S$ | | | | | MW 287.19 |
|---|---|---|---|---|---|
| Cld: C 33.45 | H 1.75 | F 26.46 | N 4.87 | O 22.28 | S 11.16% |
| Fnd: 33.67 | 1.98 | 26.27 | 5.03 | | 10.92% |

Example 22

2-Fluoro-5-(trifluoromethylsulfamoyl)-benzoic acid-(2,3,4-trihydroxy-butyl)amide (a) 2-Fluoro-5-(trifluoromethylsulfamoyl)-benzoic acid-[2-hydroxy-2-(2,2-dimethyl-1,3-dioxolan-4-yl)-ethylamide 2.87 g (10 mmol) of 2-fluoro-5-trifluoromethylsulfamoyl)- benzoic acid is dissolved in 30 ml of DMF with exclusion of moisture, 2.03 g (15 mmol) of hydroxybenzotriazole and 2.42 g (15 mmol) of 2-hydroxy-2-(2,2-dimethyl-1,3-dioxolan-4-yl)-ethylamine is added and the solution is cooled to −10° C. 3.09 g (15 mmol) of dicyclohexylcarbodiimide is added by portions to the cooled solution, it is stirred for 1 more hour at −10° C. and 5 more hours at room temperature. The precipitate of the dicyclohexylurea is then suctioned off and the filtrate is concentrated by evaporation in a vacuum. The residue is dissolved in 100 ml of ethyl acetate, the solution is shaken out with saturates bicarbonate solution and with water, dried on sodium sulfate, filtered and evaporated to dryness. 3.58 g (8.32 mmol)=83.2% of the theoretical yield is obtained as an amorphous solid.

| Analysis: $C_{15}H_{18}F_4N_2O_6S$ | | | | | MW 430.77 |
|---|---|---|---|---|---|
| Cld: C 41.86 | H 4.21 | F 17.65 | N 6.5 | O 22.3 | S 7.45% |
| Fnd: 41.63 | 4.46 | 17.87 | 6.53 | | 7.63% |

(b) 2-Fluoro-5-(trifluoromethylsulfamoyl)-benzoic acid-(2,3,4-trihydroxy-butyl)amide 2.15 g (5 mmol) of 2-fluoro-5-trifluoromethylsulfamoyl)-benzoic acid-[2-hydroxy-2-(2,2-dimethyl-1,3-dioxolan-4-yl)-ethylamide] is suspended in 20 ml of water/methanol 1:1, mixed with a catalytic amount of cation exchanger Amberlyst 15 and boiled for 3 hours. The reaction solution is filtered and the filtrate evaporated to dryness in a vacuum. 1.7 g (4.37 mmol)=87.4% of the theoretical yield is obtained as an amorphous solid.

| Analysis: $C_{12}H_{13}F_4N_2O_6S$ | | | | | MW 389.3 |
|---|---|---|---|---|---|
| Cld: | C 37.02 | H 3.36 | F 19.52 | N 7.19 | O 24.65 S 8.23% |
| Fnd: | 37.26 | 3.51 | 19.37 | 6.96 | 8.37% |

Example 23

5-Fluoro-2-[N (2,2,2-trifluoroethylsulfonyl)amido]-benzoic acid 8.62 g (45 mmol) of 2-amino-5-fluorobenzoic acid hydrochloride is dissolved or suspended in 150 ml of dichloromethane with exclusion of moisture, 5 ml of pyridine is added and the mixture is cooled to −8° C. With this temperature being maintained, a solution of 8.21 g (45 mmol) of 2,2,2-trifluoroethylsulfochloride in 20 ml of dichloromethane is instilled. Then it is stirred for 1 more hour at −8° C. and 1 more hour at room temperature. The reaction mixture is then shaken out twice with 30 ml of 2N hydrochloric acid each and twice with water, the organic phase is dried on sodium sulfate, filtered and evaporated to dryness. The residue is precipitated, partially crystalline, partially amorphous, from diethyl ether to which some pentane is added. 8.65 g (28.71 mmol)=63.8% of the theoretical yield is obtained.

| Analysis: $C_9H_7F_4NO_4S$ | | | | | MW 301.22 |
|---|---|---|---|---|---|
| Cld: | C 35.88 | H 2.34 | F 25.22 | N 4.65 | O 21.24 S 10.64% |
| Fnd: | 35.96 | 2.51 | 25.03 | 4.47 | 10.43% |

Example 24

5-Fluoro-2-[N-(2,2,2-trifluoroethylsulfonyl)amido]-benzoic acid-(2,3,4-trihydroxy-butyl)amide (a)
5-Fluoro-2-[N-(2,2,2-trifluoroethyl-sulfonyl)amido-benzoic acid-[2-hydroxy-2-(2,2-dimethyl-1,3-dioxolan-4-yl)-ethylamide]

3.01 g (10 mmol) of 5-fluoro-2-[N-(2,2,2-trifluoroethylsulfonyl)amido]-benzoic acid is dissolved in 30 ml of DMF with exclusion of moisture, 2.03 g (15 mmol) of hydroxybenzotriazole and 2.42 g (15 mmol) of 2-hydroxy-2-(2,2-dimethyl-1,3-dioxolan-4-yl)-ethylamine are added and the solution is cooled to −10° C. 3.09 g (15 mmol) of dicyclohexylcarbodiimide is added by portions to the cooled solution, it is stirred for 1 more hour at −10° C and 5 more hours at room temperature. The precipitate of the dicyclohexylurea is then suctioned off and the filtrate is concentrated by evaporation in a vacuum. The residue is dissolved in 100 ml of ethyl acetate, the solution is shaken out with saturated bicarbonate solution and with water, dried on sodium sulfate, filtered and evaporated to dryness. 3.53 g (7.95 mmol)=79.5% of the theoretical yield of the compound is obtained as an amorphous solid.

| Analysis: $C_{16}H_{20}F_4N_2O_6S$ | | | | | MW 444.4 |
|---|---|---|---|---|---|
| Cld: | C 43.24 | H 4.53 | F 17.1 | N 6.3 | O 21.6 S 10.17% |
| Fnd: | 43.55 | 4.71 | 16.87 | 6.15 | 9.75% |

(b)
5-Fluoro-2-[N-(2,2,2-trifluoroethylsulfonyl)amido]-benzoic acid-(2,3,4-trihydroxy-butyl)amide 2.22 g (5 mmol) of 5-fluoro-2-[N-(2,2,2-trifluoroethylsulfonyl)amido]-benzoic acid-[2-hydroxy-2-(2,2-dimethyl-1,3-dioxolan-4-yl)-ethylamide] is suspended in 20 ml of water/methanol 1:1, mixed with a catalytic amount of cation exchanger Amberlyst 15 and boiled for 3 hours. The reaction solution is filtered and the filtrate is evaporated to dryness in a vacuum. 1.68 g (4.17 mmol)=83.4% of the theoretical yield is obtained as an amorphous solid.

| Analysis: $C_{13}H_{15}F_4N_2O_6S$ | | | | | MW 403.33 |
|---|---|---|---|---|---|
| Cld: | C 38.71 | H 3.74 | F 18.84 | N 6.94 | O 23.8 S 7.95% |
| Fnd: | 38.92 | 3.87 | 18.56 | 7.13 | 7.72% |

Example 25

4-[N-(2,4,6-Trifluorophenyl)sulfamoyl]-benzoic acid-(2,3,4-trihydroxy-butyl)amide (a) 4-[N-(2,4,6-trifluorophenyl)sulfamoyl]-benzoic acid methyl ester 2.35 g (10 mmol) of 4-chlorosulfonyl-benzoic acid methyl ester is suspended in 30 ml of dichloromethane with exclusion of moisture, the suspension is cooled to −50° C and, at this temperature, a solution of 1.47 g (10 mmol) of 2,4,6-trifluoroaniline and 1 ml of pyridine in 20 ml of dichloromethane is instilled. When the instillation is completed, it is allowed to come to room temperature and stirred for 12 more hours. The resulting precipitate is suctioned off and extracted with ether. The ether extract and the filtrate together are concentrated by evaporation, the residue is dissolved in dichloroethane and chromatographed on silica gel 60 (Merck) with ethyl acetate/hexane. 2.71 g (7.96 mmol)=78.6% of the theoretical yield is obtained as a partially crystalline, partially amorphous product.

| Analysis: $C_{14}H_{10}F_3NO_4S$ | | | | | MW 345.3 |
|---|---|---|---|---|---|
| Cld: | C 48.69 | H 2.91 | F 16.5 | N 4.05 | O 18.53 S 9.28% |
| Fnd: | 48.43 | 3.97 | 16.32 | 3.87 | 9.44% |

(b) 4-[N-(2,4,6-Trifluorophenyl)sulfamoyl]-benzoic acid 6.22 g (18 mmol) of 4-[N-(2,4,6-trifluorophenyl)sulfamoyl]-benzoic acid methyl ester is dissolved in 50 ml of dioxane, 18 ml (32 mmol) of 2N NaOH is added and stirred for 3 hours at 50° C. The solution is then concentrated by evaporation to about 10 ml under reduced pressure, acidified with 2N hydrochloric acid and the resulting solid precipitate is suctioned off. The filter residue is dissolved in ethyl acetate, the solution is shaken out with water, dried on sodium sulfate, filtered and evaporated to dryness. 5.58 g (16.85 mmol)=76.9% of the theoretical yield is obtained as an amorphous solid.

| Analysis: $C_{13}H_8F_3NO_4S$ | | | | | MW 331.27 | |
|---|---|---|---|---|---|---|
| Cld: | C 47.13 | H 2.43 | F 17.2 | N 4.22 | O 19.31 | S 9.67% |
| Fnd: | 47.37 | 2.56 | 16.94 | 4.4 | | 9.45% |

(c) 4-[N-(2,4,6-trifluorophenyl)sulfamoyl]-benzoic acid-[2-hydroxy-2-(2,2-dimethyl-1,3-dioxolan-4-yl)-ethylamide]

4.97 g (15 mmol) of 4-[N-(2,4,6-trifluorophenyl)sulfamoyl]-benzoic acid is dissolved in 50 ml of dry dimethylformamide under argon atmosphere, 2.03 g (15 mmol) of hydroxybenzotriazole and 2.42 g (15 mmol) of 2-hydroxy-2-(2,2-dimethyl-1,3-dioxolan-4-yl)-ethylamine are added and the solution is cooled to $-10°$ C. At this temperature, 3.09 g (15 mmol) of dicyclohexylcarbodiimide is added to the solution. Then it is stirred for 1 hour at $-10°$ C. and 10 hours at room temperature. The turbid reaction solution is filtered and the filtrate is concentrated by evaporation in a vacuum. The residue is dissolved in 100 ml of ethyl acetate, the solution is shaken out five times with saturated sodium bicarbonate solution and twice with water, the organic phase is dried on sodium sulfate, filtered and concentrated by evaporation. 3.46 g (7.29 mmol)=48.6% of the theoretical yield is obtained as a solid.

| Analysis: $C_{20}H_{21}F_3N_2O_6S$ | | | | | MW 474.46 | |
|---|---|---|---|---|---|---|
| Cld: | C 50.63 | H 4.46 | F 12.01 | N 5.9 | O 20.23 | S 6.75% |
| Fnd: | 50.78 | 4.63 | 11.87 | 6.05 | | 6.83% |

(d) 4-[N-(2,4,6-Trifluorophenyl)sulfamoyl]-benzoic acid-(2,3,4-trihydroxy-butyl)amide 4.74 g (10 mmol) of 4-[N-(2,4,6-trifluorophenyl)sulfamoyl]-benzoic acid-[2-hydroxy-2-(2,2-dimethyl-1,3-dioxolan-4-yl)-ethylamide] is dissolved in a mixture of 50 ml of ethanol and 20 ml of water and the solution is acidified to pH 1 with dilute hydrochloric acid. It is stirred at this pH for 4 hours at 60° C. The solution is then adjusted to pH 6.3 with anion exchanger Amberlite IRA 67, filtered and evaporated to dryness in a vacuum. The solid amorphous residue is dried in a vacuum at 50° C. 3.4 g (7.83 mmol)=78.3% of the theoretical yield is obtained as an amorphous solid.

| Analysis: $C_{17}H_{17}F_3N_2O_6S$ | | | | | MW 434.39 | |
|---|---|---|---|---|---|---|
| Cld: | C 47.0 | H 3.94 | F 13.12 | N 6.44 | O 22.09 | S 7.38 |
| Fnd: | 47.26 | 4.12 | 12.9 | 6.23 | | 7.27% |

Example 26

3-[N (2,4,6-Trifluorophenyl)sulfamoyl]-benzoic acid-(2,3,4-trihydroxy-butyl)amide (a) 3-[N-(2,4,6-Trifluorophenyl)sulfamoyl]-benzoic acid methyl ester 2.35 g (10 mmol) of 3-chlorosulfonylbenzoic acid methyl ester is suspended in 30 ml of dichloromethane with exclusion of moisture, the suspension is cooled to $-5°$ C and at this temperature a solution of 1.47 g (10 mmol) of 2,4,6-trifluoroaniline and 1 ml of pyridine in 20 ml of dichloromethane is instilled. When the instillation is completed, it is allowed to come to room temperature and is stirred for 12 more hours. The resulting precipitate is suctioned off and extracted with ether. The ether extract and filtrate together are concentrated by evaporation and the residue is dissolved in dichloroethane and chromatographed on silica gel 60 (Merck) with ethyl acetate/hexane. 2.8 g (8.12 mmol)= 81.2% of the theoretical yield is obtained as an amorphous product.

| Analysis: $C_{14}H_{10}F_3NO_4S$ | | | | | MW 345.3 | |
|---|---|---|---|---|---|---|
| Cld: | C 48.69 | H 2.91 | F 16.5 | N 4.05 | O 18.53 | S 9.28% |
| Fnd: | 48.84 | 3.25 | 16.57 | 4.43 | | 9.03% |

(b) 3-[N-(2,4,6-Trifluorophenyl)sulfamoyl]-benzoic acid 4.49 g (13 mmol) of 3-[N-(2,4,6-trifluorophenyl)sulfamoyl]- benzoic acid dimethyl ester is dissolved in 50 ml of dioxane, 13 ml (26 mmol) of 2N NaOH is added and it is stirred for 3 hours at 50° C. The solution is then concentrated by evaporation to about 10 ml at reduced pressure, acidified with 2N hydrochloric acid and the resulting solid precipitate is suctioned off. The filter residue is dissolved in ethyl acetate, the solution is shaken out twice with water, dried on sodium sulfate, filtered and evaporated to dryness. 2.42 g (7.32 mmol)=73.2% of the theoretical yield is obtained as an amorphous solid.

| Analysis: $C_{13}H_8F_3NO_4S$ | | | | | MW 331.27 | |
|---|---|---|---|---|---|---|
| Cld: | C 47.13 | H 2.43 | F 17.2 | N 4.22 | O 19.31 | S 9.67% |
| Fnd: | 46.88 | 2.64 | 16.98 | 4.13 | | 9.83% |

(c) 3-[N-(2,4,6-Trifluorophenyl)sulfamoyl]-benzoic acid-[2-hydroxy-2-(2,2-dimethyl-1,3-dioxolan-4-yl)-ethylamide]

5.96 g (18 mmol) of 3-[N-(2,4,6-trifluorophenyl)sulfamoyl]-benzoic acid is dissolved in 50 ml of dry dimethylformamide under argon atmosphere, 2.76 g (18 mmol) of hydroxybenzotriazole and 2.9 (18 mmol) of 2-hydroxy-2-(2,2-dimethyl-1,3-dioxolan-4-yl)-ethylamine are added and the solution is cooled to $-10°$ C. At this temperature, 3.71 g (18 mmol) of dicyclohexylcarbodiimide is added to the solution. Then it is stirred for 1 hour at $-10°$ C. and 6 hours at room temperature. The turbid reaction solution is filtered and the filtrate is concentrated by evaporation in a vacuum. The residue is dissolved in 100 ml of ethyl acetate, the solution is shaken out five times with saturated sodium bicarbonate solution and twice with water, the organic phase is dried on sodium sulfate, filtered and concentrated by evaporation. The residue is chromatographed on silica gel 60 (Merck) with ethyl acetate/hexane. 4.91 g (10.35 mmol)=57.5% of the theoretical yield is obtained as an amorphous solid.

| Analysis: $C_{20}H_{21}F_3N_2O_6S$ MW 474.46 | | | | | | |
|---|---|---|---|---|---|---|
| Cld: | C 50.63 | H 4.46 | F 12.01 | N 5.9 | O 20.23 | S 6.75% |
| Fnd: | 50.55 | 4.67 | 12.19 | 6.16 | | 6.53% |

(d) 3-[N-(2,4,6-Trifluorophenyl)sulfamoyl]-benzoic acid-(2,3,4-trihydroxy-butyl)amide 4.74 g (10 mmol) of 3-[N-(2,4,6-trifluorophenyl)sulfamoyl]-benzoic acid-[2-hydroxy-2-(2,2-dimethyl-1,3-dioxolan-4-yl)-ethylamide] is dissolved in a mixture of 50 ml of ethanol and 20 ml of water and the solution is acidified to pH 1 with dilute hydrochloric acid. At this pH, it is stirred for 4 hours at 60° C. The solution is then adjusted to pH 6.6 with anion exchanger Amberlite IRA 67, filtered and evaporated to dryness in a vacuum. The solid amorphous residue is dried in a vacuum at 50° C. 3.61 g (8.32 mmol)=83.2% of the theoretical yield is obtained as an amorphous solid.

| Analysis: $C_{17}H_{17}F_3N_2O_6S$ MW 434.39 | | | | | |
|---|---|---|---|---|---|
| Cld: | C 47.0 | H 3.94 | F 13.12 | N 6.44 | O 22.09 | S 7.38% |
| Fnd: | 46.83 | 4.15 | 13.27 | 6.46 | | 7.53% |

Example 27

5-[N-(2,4,6-Trifluorophenyl)sulfamoyl]-isophthalic acid-bis(2,3,4-trihydroxy-butyl)diamide (a) 5-[N-(2,4,6-Trifluorophenyl)sulfamoyl]-isophthalic acid dimethyl ester 2.94 g (20 mmol) of 2,4,6-trifluoroaniline is dissolved in 50 ml of dichloroethane with exclusion of moisture, 3.16 g (40 mmol) of pyridine is added and the solution is cooled to 0° C. With this temperature being maintained, a solution of 5.85 g (20 mmol) of 5-chlorosulfonylisophthalic acid dimethyl ester in 50 ml of dichloroethane is instilled. It is stirred for 30 more minutes at 0° C. and 5 more hours at room temperature. The suspension is shaken out three times with 2N hydrochloric acid and twice with water, the organic phase is dried on sodium sulfate, filtered, concentrated by evaporation and the residue is chromatographed on silica gel 60 (Merck) with ethyl acetate/hexane. The fractions, concentrated by evaporation, of corresponding polarity yield 6.34 g (15.72 mmol)=78.6% of the theoretical yield is obtained as a partially crystalline product.

| Analysis: $C_{16}H_{12}F_3NO_6S$ MW 403.33 | | | | | |
|---|---|---|---|---|---|
| Cld: | C 47.64 | H 2.99 | F 14.13 | N 3.47 | O 23.8 | S 7.95% |
| Fnd: | 47.77 | 3.16 | 13.94 | 3.58 | | 8.2% |

(b) 5-[N-(2,4,6-Trifluorophenyl)sulfamoyl]-isophthalic acid 6.05 g (15 mmol) of 5-[N-(2,4,6-trifluorophenyl)sulfamoyl]-isophthalic acid dimethyl ester is dissolved in 60 ml of dioxane, 15 ml (30 mmol) of 2N NaOH is added and it is stirred for 3 hours at 50° C. The solution is then concentrated by evaporation to about 15 ml at reduced pressure, acidified with 2N hydrochloric acid and the resulting solid precipitate is suctioned off. The filter residue is dissolved in ethyl acetate, the solution is shaken out twice with water, dried on sodium sulfate, filtered and evaporated to dryness. 4.8 g (12.78 mmol)=85.22% of the theoretical yield is obtained as an amorphous solid.

| Analysis: $C_{14}H_8F_3NO_6S$ MW 375.28 | | | | | |
|---|---|---|---|---|---|
| Cld: | C 44.8 | H 2.14 | F 15.18 | N 3.73 | O 25.57 | S 8.54% |

| Analysis: $C_{14}H_8F_3NO_6S$ MW 375.28 | | | | | |
|---|---|---|---|---|---|
| Fnd: | 45.03 | 2.32 | 14.93 | 4.0 | | 8.33% |

(c) 5-[N-(2,4,6-Trifluorophenyl)sulfamoyl]-isophthalic acid-bis [2-hydroxy-2-(2,2-dimethyl-1,3-dioxolan-4-yl)-ethylamide]

4.5 g (12 mmol) of 5-[N-(2,4,6-trifluorophenyl)sulfamoyl]-isophthalic acid is dissolved in 50 ml of dry dimethylformamide under argon atmosphere, 2.03 g (15 mmol) of hydroxybenzotriazole and 2.42 (15 mmol) of 2-hydroxy-2-(2,2-dimethyl-1,3-dioxolan-4-yl)-ethylamine are added and the solution is cooled to −10° C. At this temperature, 3.09 g (15 mmol) of dicyclohexylcarbodiimide is added to the solution. It is stirred for 1 hour at −10° C. and for 8 hours at room temperature. The turbid reaction solution is filtered and the filtrate is concentrated by evaporation in a vacuum. The residue is dissolved in 100 ml of ethyl acetate, the solution is shaken out five times with saturated sodium bicarbonate solution and twice with water, the organic phase is dried on sodium sulfate, filtered and concentrated by evaporation. The residue is chromatographed on silica gel 60 (Merck) with ethyl acetate/hexane. 4.15 g (6.28 mmol)=52.33% of the theoretical yield is obtained as an amorphous solid.

| Analysis: $C_{28}H_{34}F_3N_3O_{10}S$ MW 661.65 | | | | | |
|---|---|---|---|---|---|
| Cld: | C 50.82 | H 5.18 | F 8.61 | N 6.35 | O 24.18 | S 4.84% |
| Fnd: | 51.05 | 5.32 | 8.47 | 6.23 | | 4.65% |

(d) 5-[N-(2,4,6-Trifluorophenyl)sulfamoyl]-isophthalic acid-bis (2,3,4-trihydroxybutyl)diamide 3.31 g (5 mmol) of 5-[N-(2,4,6-trifluorophenyl)sulfamoyl]-isophthalic acid-bis[2-hydroxy-2-(2,2-dimethyl-1,3-dioxolan-4-yl)-ethylamide] is dissolved in a mixture of 20 ml of ethanol and 10 ml of water and the solution is acidified to pH 1 with dilute hydrochloric acid. At this pH, it is stirred for 4 hours at 60° C. The solution is then adjusted to pH 6.4 with anion exchanger Amberlite IRA 67, filtered and evaporated to dryness in a vacuum. The solid amorphous residue is dried in a vacuum at 50° C. 2.37 g (4.07 mmol)=81.37% of the theoretical yield is obtained as an amorphous solid.

| Analysis: $C_{22}H_{26}F_3N_3O_{10}S$ MW 581.52 | | | | | |
|---|---|---|---|---|---|
| Cld: | C 45.44 | H 4.5 | F 9.8 | N 7.22 | O 27.51 | S 5.51% |
| Fnd: | 45.67 | 4.72 | 9.66 | 7.13 | | 5.77% |

Example 28

2-{N-[(4-Fluoro-2-hydroxycarbonyl)phenyl]sulfamoyl}-acetic acid-[di-(2,2,2-trifluoroethyl)amide]

(a)
2-{N-[(4-Fluoro-2-hydroxycarbonyl)phenyl]sulfamoyl}-acetic acid methyl ester 9.58 g (50 mmol) of 2-amino-4-fluoro-benzoic acid hydrochloride and 5 ml (61.8 mmol) of pyridine are put into 150 ml of dichloromethane. 8.63 g (50 mmol) of chlorosulfonyl acetic acid methyl ester, dissolved in 20 ml of dichloromethane, is instilled at 0° C. with exclusion of moisture. It is allowed to stir overnight at room temperature, the solution is washed with 2N hydrochloric acid and with water, dried on sodium sulfate and evaporated to dryness in a vacuum. The product is obtained as amorphous solid. The yield is 12.26 g (42.09 mmol) = 84.2% of the theoretical yield.

| Analysis: $C_{10}H_{10}FNO_6S$ MW 291.26 | | | | | |
|---|---|---|---|---|---|
| Cld: | C 41.24 | H 3.46 | F 6.52 | N 4.81 | S 11.01% |
| Fnd: | 41.12 | 3.51 | 6.47 | 4.88 | 10.89% |

(b)
2-{N-[(4-Fluoro-2-hydroxycarbonyl)phenyl]sulfamoyl}-acetic acid-[di-(2,2,2-trifluorethyl)amide]

230 mg (10 mmol) of sodium is dissolved in 50 ml of dry methanol and 2.91 g (10 mmol) 2-{N-[(4-fluoro-2-hydroxycarbonyl)phenyl]sulfamoyl}-acetic acid methyl ester is added to this solution. The solution is evaporated to dryness, is suspended in 10 ml of bis(2,2,2-trifluoroethyl)amine with exclusion of moisture and the suspension is refluxed for 6 hours. The excess amine is then distilled in a cold trap and the residue is dissolved in a mixture of water and ethanol. The solution is acidified by hydrochloric acid and the product precipitates as solid, which is dried in a vacuum. 3.46 g (7.86 mmol) = 78.6% of the theoretical yield is obtained.

| Analysis: $C_{13}H_{11}F_7N_2O_5S$ MW 440.3 | | | | | |
|---|---|---|---|---|---|
| Cld: | C 35.46 | H 2.52 | F 30.2 | N 6.36 | S 7.28% |
| Fnd: | 35.35 | 2.59 | 30.1 | 6.42 | 7.17% |

Example 29

5-Fluoro 2-hydroxy-3 (2,2,2-trifluoroethylcarbamoyl) benzoic acid (a) (2,6-Dibromo-4-fluoro-phenyl) benzyl ether 2.21 g (96 mmol) of sodium is dissolved in 66 ml of ethanol with exclusion of moisture. 21.6 g (80 mmol) of 2,6-dibromo-4-fluorophenol is added to this solution. A suspension results. 20.5 g (120 mmol) of benzyl bromide is added to the suspension. It is stirred for 30 minutes at room temperature and then is refluxed for 1 hour. A sample of the suspension then reacts neutrally to moist reaction paper. The precipitate of the sodium bromide is suctioned off, the filtrate is evaporated to dryness and the residue is crystallized from ethanol. 23.7 g (66 mmol) = 82.5% of the theoretical yield is obtained as a crystallizate. Melting point 83° C.

(b) 2-Benzyloxy-5-fluoro-isophthalic acid diethyl ester 10.8 g (30 mmol) of (2,6-dibromo-4-fluoro-phenyl)-benzyl ether is dissolved in 150 ml of dry tetrahydrofuran in an argon atmosphere with exclusion of moisture and the solution is cooled to −100° C. At this temperature, 225 ml (180 mmol) of a 0.8-molar solution of butyllithium in hexane is instilled. When the addition is completed, it is stirred for 5 minutes more and then a solution of 21.24 g (180 mmol) of diethylcarbonate in 50 ml of dry tetrahydrofuran is instilled. In this case, the temperature must not exceed −40° C. Then stirring is continued until the reaction mixture has reached room temperature and it is stirred for 2 more hours at this temperature. The reaction mixture is concentrated by evaporation at reduced pressure, the residue is dissolved in ethyl acetate and the solution is shaken out several times with water. The organic phase is dried on sodium sulfate, concentrated by evaporation in a vacuum and the residue is chromatographed on silica gel 60 (Merck) with ethyl acetate/hexane. 5.43 (15.69 mmol) = 52.3% of the theoretical yield of diester is obtained as an amorphous solid.

| Analysis: $C_{19}H_{19}FO_5$ MW 346.35 | | | | |
|---|---|---|---|---|
| Cld: | C 65.99 | H 5.53 | F 5.48 | O 23.09% |
| Fnd: | 66.17 | 5.77 | 5.26 | % |

(c) 2-Benzyloxy-5-fluoro-isophthalic acid monoethyl ester 25.63 g (74 mmol) of 2-benzyloxy-5-fluoroisophthalic acid diethyl ester is dissolved in 200 ml of dry ethanol with exclusion of moisture and a solution of 1.48 g of sodium hydroxide in 50 ml of ethanol is instilled into this solution in the course of 2 hours at room temperature. The monosodium salt gradually precipitates. When the instillation is completed, it is stirred for 1 hour more, the precipitate is suctioned off and the filtrate is concentrated by evaporation to about half. In this process additional monosodium salt precipitates which is also suctioned off. The two filter residues are combined, suspended in water and the suspension is acidified with concentrated hydrochloric acid. The monoacid is shaken out with ethyl acetate, the ethyl acetate solution is dried on sodium sulfate, filtered and concentrated by evaporation. The solid residue is dried in a vacuum at 50° C. 14.93 g (46.92 mmol) = 63.4% of the theoretical yield is obtained as a partially crystalline, partially amorphous solid.

| Analysis: $C_{17}H_{15}FO_5$ MW 318.3 | | | | |
|---|---|---|---|---|
| Cld: | C 64.14 | H 4.75 | F 5.96 | O 25.13% |
| Fnd: | 64.35 | 4.51 | 6.13 | % |

(d)
2-Benzyloxy-5-fluoro-3-(2,2,2-trifluoroethylcarbamoyl)-benzoic acid ethyl ester 7.96 g (25 mmol) of 2-benzyloxy-5-fluoroisophthalic acid monethyl ester in dissolved or suspended in 50 ml of dry ethyl acetate, 3.57 g (30 mmol) of thionylchloride is added and stirred for 1 hour at 50° C. The reaction solution is then evaporated to dryness under reduced pressure, the residue is evaporated twice with 50 ml of dichloromethane each and dissolved in 30 ml of dry tetrahydrofuran. This solution is mixed with 3.03 g (30 mmol) of triethylamine and then a solution of 2.97 g (30 mmol) of 2,2,2-trifluoroethylamine in 10 ml of dry tetrahydrofuran is instilled. It is stirred for 5 more hours at room temperature, the reaction solution is concentrated by evaporation to oil under reduced pressure, it is dissolved in 80 ml of ethyl acetate and shaken out twice with 10 ml of 1N hydrochloric acid each and once with 10 ml of water. The organic phase is dried on magnesium sulfate, filtered, concentrated by evaporation and the residue is chromatographed on silica gel 60 (Merck) with ethyl acetate/hexane. 7.25 g (18.15 mmol) = 72.6% of the theoretical yield of the compound is obtained as an amorphous solid.

| Analysis: $C_{19}H_{17}F_4NO_4$ MW 399.34 | | | | |
|---|---|---|---|---|
| Cld: C 57.14 | H 4.29 | F 19.03 | N 3.5 | O 16.02% |
| Fnd: 57.37 | 4.53 | 18.87 | 3.61 | % |

(e)
2-Benzyloxy-5-fluoro-3-(2,2,2-trifluoroethylcarbamoyl)-benzoic acid 10.78 g (27 mmol) of 2-benzyloxy-5-fluoro-(2,2,2-trifluoroethylcarbamoyl)-benzoic acid ethyl ester is dissolved in 60 ml of dioxane, the solution is mixed with 17.5 ml (35 mmol) of 2N sodium hydroxide solution, stirred for 1 hour at room temperature and 1 hour at 40° C. The reaction mixture is concentrated by evaporation under reduced pressure, the residue is taken up in 80 ml of water, acidified to pH 1 with concentrated hydrochloric acid. In this case, the acid precipitates mostly at amorphous solid. It is suctioned off and washed with a little water. The aqueous phase is shaken out several times with ethyl acetate. The ethyl acetate extract is concentrated by evaporation and the residue is combined with the precipitate from the water. It is dried in a vacuum for 48 hours at 50° C. Yield: 8.38 g (22.57 mmol) =83.6% of the theoretical yield is obtained as an amorphous solid.

| Analysis: $C_{17}H_{13}F_4NO_4$ MW 371.29 | | | | |
|---|---|---|---|---|
| Cld: C 54.99 | H 3.52 | F 20.46 | N 3.77 | O 17.23% |
| Fnd: 55.22 | 3.78 | 20.27 | 3.58 | % |

(f)
5-Fluoro-2-hydroxy-3-(2,2,2-trifluoroethylcarbamoyl)-benzoic acid 5.2 g (14 mmol) of 2-benzyloxy-5-fluoro-3-(2,2,2-trifluoroethylcarbamoyl)-benzoic acid is dissolved in 30 ml of ethanol. 250 mg of palladium-carbon (10%) is added and is hydrogenated in 1 hour at normal temperature. The catalyst is then filtered off and the filtrate is evaporated to dryness in a vacuum. The residue is chromatographed on silica gel 60 (Merck) with dichloromethane/methanol. 3.03 g (11.34 mmol)=81% of the theoretical yield of the compound is obtained as an amorphous solid.

| Analysis: $C_{10}H_7F_4O_4$ MW 267.16 | | | | |
|---|---|---|---|---|
| Cld: C 44.95 | H 2.64 | F 28.44 | | O 23.95% |
| Fnd: 44.76 | 2.83 | 28.21 | | % |

Example 30

5-Fluoro-2-hydroxy-3-(2,2,2-trifluoroethylcarbamoyl)-benzoic acid-(2,3,4-trihydroxy-butyl)amide (a)
2-Benzyloxy-5-fluoro-3-(2,2,2-trifluoroethylcarbamoyl)-benzoic acid-[2-hydroxy-2-(2,2-dimethyl-1,3-dioxolan-4-yl)-ethylamide]

4.46 g (12 mmol) of 2-benzyloxy-5-fluoro-3-(2,2,2-trifluoroethylcarbamoyl)-benzoic acid is dissolved in 30 ml of dry N,N-dimethylformamide with exclusion of moisture, 1.85 g (12 mmol) of hydroxybenzotriazolel, 2.43 g (15 mmol) of 2-hydroxy-2-(2,2-dimethyl-1,3-dioxolan-4-yl)-ethylamine are added and the solution is cooled to −10° C. 2.68 g (13 mmol) of dicyclohexylcarbodiimide is added by portions to the cooled solution, it is stirred for 1 hour at −10° C. and 6 hours at room temperature. The precipitate of the dicyclohexylurea is then suctioned off, the filtrate is evaporated to dryness in a vacuum and the residue is dissolved in about 100 ml of ethyl acetate. The solution is shaken out with saturated bicarbonate solution and with water, dried on sodium sulfate, filtered and concentrated by evaporation and chromatographed on silica gel 60 (Merck) with ethyl acetate/hexane. 4.22 g (8.2 mmol)=68.3% of the theoretical yield of the compound is obtained as an amorphous solid.

| Analysis: $C_{24}H_{26}F_4N_2O_6$ MW 514.47 | | | | |
|---|---|---|---|---|
| Cld: C 56.03 | H 5.09 | F 14.77 | N 5.44 | O 18.65% |
| Fnd: 55.81 | 4.9 | 14.92 | 5.23 | % |

(b)
5-Fluoro-2-hydroxy-3-(2,2,2-trifluoroethylcarbamoyl)-benzoic acid-(2,3,4-trihydroxybutyl)amide 6.95 g (13.5 mmol) of 2 benzyloxy-5-fluoro-3-(2,2,2-trifluoroethylcarbamoyl)-benzoic acid-[2-hydroxy-2-(2,2-dimethyl-1,3-dioxolan-4-yl)-ethylamide] is dissolved in 20 ml of methanol, 5 ml of water and 5 ml of IN hydrochloric acid is added and stirred for 3 hours at room temperature. The solution is then adjusted to pH 6.3 by addition of anion exchanger Amberlite IRA 67, 200 mg of palladium-carbon (10%) is added and hydrogenated for 1 hour at normal pressure. The catalyst is then filtered off, the filtrate is evaporated to dryness in a vacuum and the residue is chromatographed on silica gel 60 (Merck) with dichloromethane/methanol. 3.76 g (9.77 mmol)=72.4% of the theoretical yield of the compound is obtained as an amorphous solid.

| Analysis: $C_{14}H_{16}F_4N_2O_6$ MW 384.28 | | | | |
|---|---|---|---|---|
| Cld: C 43.75 | H 4.19 | F 19.77 | N 7.29 | O 24.98% |
| Fnd: 43.96 | 4.32 | 19.58 | 7.13 | % |

Example 31

5-Fluoro-2-hydroxy-3-(2,2,2-trifluoroethylcarbamoyl)-benzoic acid-N methyl-N-(2,3,4-trihydroxy-butyl)amide (a)
2-Benzyloxy-5-fluoro-3-(2,2,2-trifluoroethylcarbamoyl)-benzoic acid-N-methyl-N-[2-hydroxy-2-(2,2-dimethyl-1,3-dioxolan-4-yl)-ethylamide]

2.97 g (8 mmol) of 2-benzyloxy-5-fluoro-3-(2,2,2-trifluoroethylcarbamoyl)-benzoic acid is dissolved in 20 ml of dry N,N-dimethylformamide with exclusion of moisture, 1.08 g (8 mmol) hydroxybenzotriazole, 1.76 g (10 mol) of N-methyl-[2-hydroxy-2-(2,2-dimethyl-1,3-dioxolan-4-yl)-ethylamine are added and the solution is cooled to −10° C. 1.85 g (9 mmol) dicyclohexylcarbodiimide is added by portions to the cooled solution, it is stirred for 1 hour at −10° C and 5 hours at room temperature. The precipitate of the dicyclohexylurea is then suctioned off, the filtrate is evaporated to dryness in a vacuum and the residue is dissolved in about 100 ml of ethyl acetate. The solution is shaken out with saturated bicarbonate solution and with water, dried on sodium sulfate, filtered, concentrated by evaporation and chromatographed on silica gel 60 (Merck) with ethyl acetate/hexane. 2.69 g (5.09 mmol)=63.6% of the theoretical yield of the compound is obtained as an amorphous solid.

| Analysis: $C_{25}H_{28}F_4N_2O_6$ MW 528.5 | | | | | |
|---|---|---|---|---|---|
| Cld: | C 56.81 | H 5.34 | F 14.37 | N 5.3 | O 18.16% |
| Fnd: | 56.64 | 5.47 | 14.51 | 5.43 | % |

(b)
5-Fluoro-2-hydroxy-3-(2,2,2-trifluoroethylcarbamoyl)-benzoic acid-N-methyl-N-(2,3,4-trihydroxy-butyl)amide 3.86 g (7.3 mmol) of 2-benzyloxy-5-fluoro-3-(2,2,2-trifluoroethylcarbamoyl)-benzoic acid-N-methyl-N-[2-hydroxy-2-(2,2-dimethyl-1,3-dioxolan-4-yl)-ethylamide] is dissolved in 10 ml of methanol. 10 ml of water and 200 mg of anion exchanger Amberlite 15 are added and refluxed for 2 hours. The ion exchanger is then filtered off, 150 mg of palladium-carbon (10%) is added to the filtrate and hydrogenated for 1 hour at normal pressure. The catalyst is then filtered off, the filtrate is evaporated to dryness in a vacuum and the residue is chromatographed on silica gel 60 (Merck) with dichloromethane/ methanol. 2.16 g (5.42 mmol)=74.3% of the theoretical yield of the compound is obtained as an amorphous solid.

| Analysis: $C_{15}H_{18}F_4N_2O_6$ MW 398.31 | | | | | |
|---|---|---|---|---|---|
| Cld: | C 45.23 | H 4.55 | F 19.07 | N 7.03 | O 24.1% |
| Fnd: | 45.47 | 4.4 | 18.81 | 6.87 | % |

Example 32

5-Fluoro-2-hydroxy-3-(trifluoromethyl) benzoic acid (a) 2-Bromo-4-fluoro-6(trifluoromethyl)-phenol 9 g (500 mmol) of 4-fluoro-2-(trifluoromethyl)-phenol is dissolved in 100 ml of dichloroethane, the solution is stirred at 50° C. and a solution of 9.6 g (60 mmol) of bromine in 30 ml of dichloroethane is instilled in the course of 2 hours. When the instillation is completed, it is stirred for 1 more hour at 50° C. and then concentrated by evaporation in a vacuum. The oily residue is dissolved in 100 ml of dichloroethane and shaken out three times with 20 ml of water each. The organic phase is dried on magnesium sulfate, filtered, concentrated by evaporation and the residue is chromatographed on silica gel 60 (Merck) ethyl acetate/hexane. 8.07 g (31.15 mmol)=62.3% of the theoretical yield is obtained as a partially crystalline solid.

| Analysis: $C_7H_3BrF_4O$ MW 259.0 | | | | | |
|---|---|---|---|---|---|
| Cld: | C 32.46 | H 1.16 | Br 30.85 | F 29.34 | O 6.17% |
| Fnd: | 32.23 | 1.05 | 31.03 | 29.11 | % |

(b)
[2-Bromo-4-fluoro-6-(trifluoromethyl)-phenyl]-benzyl ether 0.65 g (28 mmol) of sodium is dissolved in 35 ml of dry ethanol, 5.96 g (23 mmol) of 2-bromo-4-fluoro-6-(trifluoromethyl)-phenol is added and it is stirred for 20 minutes at room temperature, 7.17 g (42 mmol) of benzyl bromide is added and refluxed for 1 hour. Sodium bromide precipitates out crystalline from the solution The hot solution is filtered, the filtrate is evaporated to dryness and the residue is chromatographed on silica gel 60 with dichloromethane/hexane. 6.29 g (18 mmol) =78.3% of the theoretical yield is obtained as a predominantly crystalline solid.

| Analysis: $C_{14}H_9BrF_4O$ MW 349.13 | | | | | |
|---|---|---|---|---|---|
| Cld: | C 48.16 | H 2.59 | Br 22.88 | F 21.76 | O 4.58% |
| Fnd: | 48.33 | 2.73 | 22.67 | 21.59 | % |

(c) 2-Benzyloxy-5-fluoro-3-(trifluoromethyl)-benzoic acid ethyl ester 6.11 g (17.5 mmol) of 2-bromo-4-fluoro-6-(trifluoromethyl)-phenyl]-benzyl ether is dissolved in 60 ml of dry tetrahydrofuran in an argon atmosphere with exclusion of moisture and the solution is cooled to −100° C. At this temperature, 65.63 ml (52.5 mmol) of a 0.8-molar solution of butyllithium in hexane is instilled. When the addition is completed, it is stirred for 5 more minutes and then a solution of 3.54 g (30 mmol) of diethylcarbonate in 20 ml of dry tetrahydrofuran is instilled. In this case, the temperature is kept under −40° C. Then stirring is continued until the reaction mixture reaches room temperature, and it is stirred for 3 more hours at this temperature. The reaction mixture is concentrated by evaporation under reduced pressure, the residue is dissolved in ethyl acetate and the solution is shaken out several times with water. The organic phase is dried on magnesium sulfate, concentrated by evaporation in a vacuum and the residue is chromatographed on silica gel 60 (Merck) with ethyl acetate/-hexane. 5.43 g (10.26 mmol)=58.6% of the theoretical yield of the compound is obtained as an amorphous solid.

| Analysis: $C_{17}H_{14}F_4O_3$ MW 342.29 | | | | |
|---|---|---|---|---|
| Cld: | C 59.65 | H 4.12 | F 22.2 | O 14.02% |
| Fnd: | 59.83 | 4.27 | 21.93 | % |

(d) 5-Fluoro-2-hydroxy-3-(trifluoromethyl)-benzoic acid 4.28 g (12.3 mmol) of 2-benzyloxy-5-fluoro-3-(trifluoromethyl)-benzoic acid ethyl ester is dissolved in 20 ml of dioxane, 7.5 ml (15 mmol) of 2N sodium hydroxide solution is added and it is stirred for 1 hour at 50° C. The reaction solution is then mixed with 200 mg of palladium-carbon (10%) and hydrogenated for 1 hour at normal temperature. The catalyst is then filtered off, the alkaline filtrate is mixed with 30 ml of water and extracted with dichloromethane. The aqueous phase is acidified to pH 1 with concentrated hydrochloric acid and extracted with ethyl acetate. The ethyl acetate extract is dried on magnesium sulfate, filtered and evaporated to dryness. The crystalline residue is dried in a vacuum at 50° C. for 24 hours. 2.27 g (10.15 mmol)=82.5% of the theoretical yield is obtained. Melting range 76–83° C.

| Analysis: $C_8H_4F_4O_3$ MW 224.11 | | | | |
|---|---|---|---|---|
| Cld: | C 42.87 | H 1.79 | F 33.9 | O 21.41% |
| Fnd: | 42.66 | 1.93 | 33.76 | % |

Example 33

5-Fluoro-2-hydroxy-3-(trifluoromethyl)-benzoic acid-(2,3,4-trihydroxy-butyl)amide (a) 2-Benzyloxy-5-fluoro-(trifluoromethyl)-benzoic acid-[2-hydroxy-2-(2,2-dimethyl-1,3-dioxolan-4-yl)-ethylamide]

3.42 g (10 mmol) of 2-benzyloxy-5-fluoro-3-(trifluoromethyl)-benzoic acid ethyl ester is dissolved in 10 ml of ethanol, 2.43 g (15 mmol) of 2-hydroxy-2-(2,2-dimethyl-1,3-dioxolan-4-yl)-ethylamine is added, the ethanol is distilled off and the remaining oil is warmed to 100° C. in a vacuum in 2 hours. The reaction mixture is then dissolved in 50 ml of ethyl acetate, shaken out twice with 10 ml of 1N hydrochloric acid each, the organic phase is dried on sodium sulfate, concentrated by evaporation and the residue is chromatographed on silica gel 60 with ethyl acetate/hexane. 2.18 g (7.18 mol) = 47.68% of the theoretical yield is obtained as an amorphous solid.

| Analysis: $C_{22}H_{23}F_4NO_5$ MW 457.42 | | | | |
|---|---|---|---|---|
| Cld: | C 57.76 | H 5.06 | F 16.61 | N 3.06 | O 17.48% |
| Fnd: | 57.92 | 5.23 | 16.45 | 2.87 | % |

(b) 5-Fluoro-2-hydroxy-3-(trifluoromethyl)-benzoic acid-(2,3,4-trihydroxy-butyl)amide 6.86 g (15 mmol) of 5-fluoro-2-hydroxy-3-(trifluoromethyl)-benzoic acid-[2-hydroxy-2-(2,2-dimethyl-1,3-dioxolan-4-yl)-ethylamide] is dissolved in 30 ml of methanol, 30 ml of water and 300 mg of cation exchanger Amberlyst 15 are added and refluxed for 2 hours. The ion exchanger is then filtered off, 250 mg of palladium-carbon (10%) is added to the filtrate and hydrogenated for 1 hour at normal pressure. The catalyst is then filtered off, the filtrate is evaporated to dryness in a vacuum and the residue is chromatographed on silica gel 60 (Merck) with dichloromethane/methanol. 3.08 mg (9.41 mmol) = 62.7% of the theoretical yield of the compound is obtained as an amorphous solid.

| Analysis: $C_{12}H_{13}F_4NO_5$ MW 327.23 | | | | |
|---|---|---|---|---|
| Cld: | C 44.04 | H 4.0 | F 23.22 | N 4.28 | O 24.44% |
| Fnd: | 43.88 | 4.16 | 22.95 | 4.43 | % |

Example 34

5-Fluoro 2-hydroxy-3-(trifluoromethyl)-benzoic acid-N-methyl N-(2,3,4-trihydroxy-butyl)amide (a) 2-Benzyloxy-5-fluoro-3-(trifluoromethyl)-benzoic acid-N-methyl-N-[2-hydroxy-2-(2,2-dimethyl-1,3-dioxolan-4-yl)-ethylamide]

4.66 g (13.6 mmol) of 2-benzyloxy-5-fluoro-3-(trifluoromethyl)-benzoic acid ethyl ester is dissolved in 15 ml of ethanol, 3.59 g (20.4 mmol) of N-methyl-N-[2-hydroxy-2-(2,2-dimethyl-1,3-dioxolan-4-yl)-ethylamine is added, the ethanol is distilled off and the remaining oil is warmed in a vacuum to 100° C. in 2 hours. Then the reaction mixture is dissolved in 80 ml of ethyl acetate, shaken out twice with 10 ml of 1N hydrochloric acid each, the organic phase is dried on magnesium sulfate, concentrated by evaporation and the residue is chromatographed on silica gel 60 with ethyl acetate/hexane. 3.31 g (7.03 mmol) = 5.17% of the theoretical yield is obtained as an amorphous solid.

| Analysis: $C_{23}H_{25}F_4NO_5$ MW 471.45 | | | | |
|---|---|---|---|---|
| Cld: | C 58.59 | H 5.34 | F 16.11 | N 2.97 | O 16.96% |
| Fnd: | 58.47 | 5.51 | 15.92 | 3.11 | % |

(b) 5-Fluoro-2-hydroxy-3-(trifluoromethyl)-benzoic acid-N-methyl-N-(2,3,4-trihydroxy-butyl)amide 8.01 g (17 mmol) of 5-fluoro-2-hydroxy-3-(trifluoromethyl)-benzoic acid-N-methyl-N-[2-hydroxy-2-(2,2-dimethyl-1,3-dioxolan-4-yl)-ethylamide] is dissolved in 35 ml of methanol, 35 ml of water and 350 mg of cation exchanger Amberlyst 15 are added and refluxed for 2 hours. The ion exchanger is then filtered off, 350 mg of palladium-carbon (10%) is added to the filtrate and is hydrogenated for 1 hour at normal pressure. The catalyst is then filtered off, the filtrate is evaporated to dryness in a vacuum and the residue is chromatographed on silica gel 60 (Merck) with dichloromethane/methanol. 3.9 g (11.44 mmol) = 67.3% of the theoretical yield of the compound is obtained as an amorphous solid.

| Analysis: $C_{13}H_{15}F_4NO_5$ MW 341.26 | | | | |
|---|---|---|---|---|
| Cld: | C 45.75 | H 4.43 | F 22.26 | N 4.1 | O 23.44% |
| Fnd: | 46.03 | 4.57 | 21.98 | 4.22 | % |

Example 35

Hexafluoroglutaric acid bis[(5-fluoro 2-hydroxy 3-hydroxycarbonyl)-anilide (a) Hexafluoroglutaric acid bis[(2-hydroxy-3-hydroxycarbonyl-5-nitro)-anilide 9.91 g (50 mmol) of 3-amino-2-hydroxy-5-nitrobenzoic acid (J. Chem. Soc. 111, 540 [1917]) is dissolved in 30 ml of dry dimethylformamide, 10.12 g (0.1 mmol) of triethylamine is added, the solution is cooled to 0° C. and 6.9 (25 mmol) of hexafluoroglutaric acid dichloride is instilled at this temperature. It is stirred for 30 minutes more at 0° C. and 3 hours at room temperature. The precipitate of triethylamine hydrochloride is suctioned off and the filtrate is precipitated in 300 ml of dichloromethane. The precipitate is suctioned off, dissolved in methanol and chromatographed on silica gel 60 with dichloromethane/methanol. 13.09 g (21.8 mmol) = 43.6% of the theoretical yield of the compound is obtained as a partially amorphous, partially crystalline solid.

| Analysis: $C_{19}H_{10}F_6N_4O_{12}$ MW 600.3 | | | | |
|---|---|---|---|---|
| Cld: | C 38.01 | H 1.67 | F 18.98 | N 9.98 | O 31.98% |
| Fnd: | 37.8 | 1.83 | 19.2 | 9.75 | % |

(b) Hexafluoroglutaric acid-bis[(2-hydroxy-3-ethoxycarbonyl-5-nitro)-anilide]

12 g (20 mmol) of hexafluoroglutaric acid-bis[(2-hydroxy-3-hydroxycarbonyl-5-nitro)-anilide]is dissolved in 120 ml of dry ethanol, 2 ml of concentrated sulfuric acid is added and the solution is refluxed for 6 hours The sulfuric acid is buffered out by addition of solid sodium bicarbonate until the supernatant solution shows a pH 8 on water-moistened pH paper. The solid is suctioned off and the filtrate evaporated to dryness The residue is chromatographed on silica gel 60 with hexane/ethyl acetate. 7.04 g (10.72 mmol)=53.6% of the theoretical yield is obtained as an amorphous solid.

| Analysis: $C_{23}H_{18}F_6N_4O_{12}$ MW 656.14 | | | | |
|---|---|---|---|---|
| Cld: | C 42.08 | H 2.76 | F 17.36 | N 8.53 | O 29.24% |
| Fnd: | 42.25 | 2.93 | 17.13 | 8.38 | % |

(c) Hexafluoroglutaric acid-bis[(2-benzyloxy-3-ethoxycarbonyl-5-nitro)-anilide]

1.5 g (65 mmol) of sodium is dissolved in 100 ml of dry ethanol in a nitrogen atmosphere with exclusion of moisture. 17.7 g (27 mmol) of hexafluoroglutaric acid-bis[(2-hydroxy-3-ethoxycarbonyl-5-nitro)-anilide] is added to this solution, is stirred for 15 minutes at room temperature, 11.12 g (65 mmol) of benzylbromide is added and refluxed for 4 hours. The reaction solution is evaporated to dryness, the residue is taken up in ethyl acetate, filtered and the filtrate is chromatographed on silica gel 60 with hexane/ethyl acetate. 10.73 g (12.83 mmol)=47.5% of the theoretical yield of the compound is obtained as an amorphous solid.

| Analysis: $C_{37}H_{30}F_6N_4O_{12}$ MW 836.65 | | | | |
|---|---|---|---|---|
| Cld: | C 53.11 | H 3.61 | F 13.62 | N 6.69 | O 22.94% |
| Fnd: | 53.32 | 3.77 | 13.48 | 6.5 | % |

(d) Hexafluoroglutaric acid-bis[(5-amino-2-benzyloxy-3-ethoxycarbonyl)-anilide]

8.37 g (10 mmol) of hexafluoroglutaric acid-bis[(2-benzyloxy-3-ethoxycarbonyl-5-nitro)-anilide] is dissolved in 84 mg of ethanol, 11.3 g (50 mmol) of tin(II) chloride·H₂O is added and the suspension is stirred for 4 hours at 70° C. bath temperature. The reaction mixture is concentrated by evaporation to an oil and the latter is chromatographed on silica gel 60 with dichloromethane/ethyl acetate. 5.64 g (7.26 mmol)=72.6% of the compound is obtained as amorphous solid.

| Analysis: $C_{37}H_{34}F_6N_4O_8$ MW 776.69 | | | | |
|---|---|---|---|---|
| Cld: | C 57.21 | H 4.41 | F 14.67 | N 7.21 | O 16.47% |
| Fnd: | 57.43 | 4.6 | 14.43 | 6.96 | % |

(e) Hexafluoroglutaric acid-bis[(2-benzyloxy-3-ethoxycarbonyl-5-fluoro)-anilide]

9.32 g (12 mmol) of hexafluoroglutaric acid-bis[(5-amino-2-benzyloxy-3-ethoxycarbonyl)-anilide] is suspended in a mixture of 9.6 ml (60 mmol) of 42% tetrafluoroboric acid and 10 ml of water. A solution of 2.07 g (30 mmol) of sodium nitrite in 10 ml of water is instilled in this suspension at 10°-15° C. internal temperature. It is stirred for 30 minutes at 0°-5° C., the precipitate is suctioned off, washed with 20 ml of cold 5% tetrafluoroboric acid, 20 ml of cold ethanol and 50 ml of cold ether. The salt is then suspended in 100 ml of m-xylene and the suspension is gradually heated to boiling in the course of about 2 hours. The xylene is distilled off under reduced pressure. The residue is taken up in 50 ml of ethanol, 1.5 ml of concentrated sulfuric acid is added and it is refluxed for 3 hours. It is cooled to room temperature, sodium bicarbonate is added until the supernatant exhibits a neutral pH and the precipitate is filtered off. The filtrate is predominantly concentrated by evaporation and the residue is chromatographed on silica gel 60 with dichloromethane/ethyl acetate. 3.34 g (4.27 mmol)=35.6% of the theoretical yield of the compound is obtained as an amorphous solid.

| Analysis: $C_{37}H_{30}F_8N_2O_8$ MW 782.64 | | | | |
|---|---|---|---|---|
| Cld: | C 56.78 | H 3.86 | F 19.42 | N 3.57 | O 16.35% |
| Fnd: | 56.62 | 4.03 | 19.23 | 3.43 | % |

(f) Hexafluoroglutaric acid-bis[(5-fluoro-2-hydroxy-3-hydroxycarbonyl)-anilide]

5.87 g (7.5 mmol) of hexafluoroglutaric acid-bis[(2-benzyloxy-3-ethoxycarbonyl-5-fluoro)-anilide] is dissolved in 25 ml of dioxane, 150 mg of Pd-carbon (10%) is added and hydrogenated for 2 hours at normal pressure. The catalyst is suctioned off and the filtrate is stirred with 15 ml of 2N sodium hydroxide solution for 2 hours at 50° C. The solution is adjusted to about pH 8 with concentrated hydrochloric acid and largely concentrated by evaporation in a vacuum. The oily residue is dissolved in water and acidified to pH 1. The product precipitates mostly as amorphous precipitate. The aqueous phase is shaken out with chloroform. Precipitate and chloroform are combined, concentrated by evaporation and the residue is chromatographed on silica gel 60 with dichloromethane/acetone. (4.76 mmol)=63.4% of the theoretical yield is obtained as an amorphous solid.

| Analysis: $C_{19}H_{10}F_8N_2O_8$ MW 546.26 | | | | |
|---|---|---|---|---|
| Cld: | C 41.77 | H 1.84 | F 27.82 | N 5.12 | O 23.43% |
| Fnd: | 41.96 | 2.04 | 27.66 | 4.93 | % |

Example 36

Hexafluoroglutaric acid-bis([5-fluoro 2 hydroxy-3-(2,3,4-trihydroxybutylcarbamoyl]-anilide 5.0 g (6.4 mmol) of hexafluoroglutaric acid-bis[(5-amino-2-benzyloxy-3-ethylcarbonyl)-anilide] is dissolved in 15 ml of ethanol, 3.24 g (20 mmol) of 2-hydroxy-2-(2,2-dimethyl-1,3-dioxolan-4-yl)-ethylamine is added, the ethanol is distilled off and the remaining oil is warmed to about 100°-110° C. for 3 hours in a vacuum. The reaction mixture is then cooled to room temperature, taken up in acetone and chromatographed on silica gel 60 with hexane/acetone. The combined fractions of the intermediate product is concentrated by evaporation with benzyl and ketal protecting groups and the residue is dissolved in 50 methanol 200 mg of Pd-carbon (10%) is added to this solution and hydrogenated for 2 hours at normal pressure. The catalyst is filtered off, 30 ml of water and 500 mg of cation exchanger Amberlyst 15 are added to the filtrate and it is stirred for 3 hours at 60° C. The ion exchanger is then filtered off, the filtrate is evaporated to dryness in a vacuum and the residue is chromatographed on silica gel with dichloromethane/methanol. 2 g (2.66 mmol)=41.5% of the theoretical yield is obtained as an amorphous solid.

| Analysis: $C_{27}H_{28}F_8N_4O_{12}$ MW 752.52 | | | | |
|---|---|---|---|---|
| Cld: | C 43.29 | H 3.75 | F 20.19 | N 7.44 | O 25.51% |
| Fnd: | 43.42 | 3.9 | 19.93 | 7.27 | % |

Example 37

5-Fluoro-3-hydroxacetamido-2-hydroxy-benzoic acid-(2,2,2,-trifluoro ethyl)amide (a) 5-Fluoro-3-nitro-salicylic acid 6.24 g (40 mmol) of 5-fluoro-salicylic acid is dissolved in 62.4 ml of acetonitrile with warming, the solution is cooled to 0° C. and, with this temperature being maintained a solution of 2.96 ml (44 mmol) of 65% $HNO_3$ in 14.8 ml of acetonitrile is instilled. The reaction mixture is stirred for 24 hours at 0° C., then filtered over 7.5 g of silica gel 60 and evaporated to dryness 6.1 g =75.8% of the theoretical yield is obtained of the crude product, which is used in the next reaction without purification.

(b) 5-Fluoro-2-hydroxy-3-nitro-benzoic acid-(2,2,2-trifluoro-ethyl)amide 5.4 g (26.85 mmol) of 5-fluoro-2-hydroxy-3-nitrobenzoic acid is suspended in 27 ml of thionylchloride and is stirred at 50° C. An almost clear solution results. After 1 hour, the solution is evaporated to dryness in a vacuum, the residue is dissolved in 27 ml of THF and 27 ml of 2,2,2-trifluoroethylamine is added. The solution is stirred for 15 hours at room temperature, then filtered, the filtrate is concentrated by evaporation and chromatographed on silica gel 60 with methylene chloride/ethyl acetate. 3.51 g=46.33% of the theoretical yield is obtained as an amorphous solid. It can be crystallized from dioxane.

| Analysis: $C_9H_6F_4N_2O_4$ MW 282.15 | | | | |
|---|---|---|---|---|
| Cld: | C 38.31 | H 2.14 | F 26.93 | N 9.92 | O 22.68% |
| Fnd: | 38.05 | 2.32 | 26.65 | 9.63 | |

(c) 3-Amino-5-fluoro-2-hydroxy-benzoic acid-(2,2,2,-trifluoro-ethyl)amide 7.05 g (25 mmol) of 5-fluoro-2-hydroxy-3-nitrobenzoic acid-(2,2,2,-trifluoro-ethyl)amide is dissolved in 70 ml of ethanol, 5.65 (25 mmol) of $SnCl_2 \cdot H_2O$ is added and the suspension is stirred for 2 hours at 70° C. The reaction mixture is then concentrated by evaporation to oil and used in the next reaction without purification.

(d) 3-Acetoxyacetamido-5-fluoro-2-hydroxy-benzoic acid-(2,2,2,-trifluoro-ethyl)amide 6.3 (25 mmol) of crude 3-amino-5-fluoro-2-hydroxybenzoic acid-(2,2,2,-trifluoro-ethyl)amide is dissolved in 30 ml of THF, 3.04 g (30 mmol) of triethylamine as well as 4.1 g (30 mmol) of acetoxyacetylchloride are added and stirred for 12 hours at room temperature. The reaction solution is then concentrated by evaporation in a vacuum and the residue is chromatographed on silica gel 60 with ethyl acetate/hexane. 5.52 g=62.7% of the theoretical yield is obtained as an amorphous solid.

| Analysis: $C_{13}H_{12}F_4N_2O_5$ MW 352.24 | | | | |
|---|---|---|---|---|
| Cld: | C 44.32 | H 3.43 | F 21.57 | N 7.95 | O 22.71% |
| Fnd: | 44.67 | 3.52 | 21.31 | 7.78 | |

(e) 5-Fluoro-3-hydroxyacetamido-2-hydroxy-benzoic acid-(2,2,2,-trifluoro-ethyl)amide 5.9 g (17 mmol) of 3-acetoxyacetamido-5-fluoro-2-hydroxy-benzoic acid-(2,2,2,-trifluoro-ethyl)amide is dissolved in 34 ml of 1N NaOH and stirred for 30 minutes at 40° C. The reaction solution is then cooled to room temperature and filtered over 200 ml of cation exchanger. The eluate is evaporated to dryness in a vacuum and the residue is chromatographed on silica gel 60 with ethyl acetate/acetone. 3.3 g=62.7% of the theoretical yield is obtained as an amorphous material.

| Analysis: $C_{11}H_{10}F_4N_2O_4$ | | | | |
|---|---|---|---|---|
| Cld: | C 42.59 | H 3.24 | F 24.49 | N 9.03 | O 20.63% |
| Fnd: | 42.83 | 3.52 | 24.21 | 8.87 | |

Example 38

5-Fluoro-3-[N-(2,3-dihydroxy-propyl)-hydroxyacetamido-2-hydroxy-benzoic acid-(2,2,2,-trifluoro-ethyl)amide (a) 5-Fluoro-3-acetoxyacetamido-2-benzyloxybenzoic acid-(2,2,2,-trifluoro-ethyl)amide 7.75 g (22 mmol) of 3-acetoxyacetamido-5-fluoro-2-hydroxy-benzoic acid-(2,2,2,-trifluoro-ethyl)amide (Example 37d) is dissolved in 50 ml of dry THF. 1.35 g (25 mmol) of sodium methylate is added, stirred for 15 minutes at room temperature, 4.27 g (25 mmol) of benzylbromide is added and refluxed for 1 hour. The reaction solution is then cooled to room temperature, NaBr is filtered off, the filtrate is concentrated by evaporation in a vacuum and the residue is chromatographed on silica gel 60 with ethyl acetate/hexane. 5.2 g=53.4% of the theoretical yield is obtained as an amorphous solid.

| Analysis: $C_{20}H_{18}F_4N_2O_5$ MW 442.37 | | | | |
|---|---|---|---|---|
| Cld: | C 54.3 | H 4.1 | F 17.17 | N 6.33 | O 18.08% |
| Fnd: | 54.57 | 4.32 | 16.88 | 6.17 | |

(b)
5-Fluoro-3-[N-(2,2-dimethyl-1,3-dioxolan-4-ylmethyl)-acetoxyacetamido-2-benzyloxy-benzoic acid-(2,2,2,-trifluoro-ethyl)amide 6.64 g (15 mmol) of 5-fluoro-3-acetoxyacetamido-2-benzyloxy-benzoic acid-(2,2,2,-trifluoro-ethyl)amide is dissolved in 50 ml of THF, 480 mg (20 mmol) of NaH is added, it is stirred for 30 minutes at room temperature, 3.01 g (20 mmol) of 4-chloromethyl-2,2-dimethyl-dioxolane is added and refluxed for 3 hours. The reaction solution is then concentrated by evaporation in a vacuum and the residue is chromatographed on silica gel 60 with ethyl acetate/hexane. 4.03 g=48.3% of the theoretical yield is obtained as an amorphous solid.

| Analysis: $C_{26}H_{28}F_4N_2O_7$ MW 556.51 | | | | |
|---|---|---|---|---|
| Cld: | C 56.11 | H 5.07 | F 13.65 | N 5.07 | O 20.12% |
| Fnd: | 56.32 | 5.32 | 13.44 | 4.93 | |

(c)
5-Fluoro-3-[N-(2,3-dihydroxy-propyl)-hydroxyacetamido-2-hydroxy benzoic acid-(2,2,2,-trifluoro-ethyl)amide 6.68 g (12 mmol) of 5-fluoro-3-[N-(2,2-dimethyl-1,3-dioxolan-4-ylmethyl)-acetoxyacetamido-2-benzyloxy-benzoic acid- (2,2,2,-trifluoro-ethyl)amide is dissolved in 40 ml of methanol, 15 ml of 1N methanolic NaOH is added and it is stirred for 30 minutes at 40° C. The solution is then stirred for 3 hours with 40 ml of ion exchanger Amberlyst 15 at room temperature, filtered, the filtrate is concentrated by evaporation in a vacuum, the residue is dissolved in 40 ml of methanol, 200 mg of palladium-carbon (10%) is added and hydrogenated for 1 hour at normal pressure. The catalyst is then suctioned off, the filtrate is evaporated to dryness and the residue is chromatographed on silica gel 60 with methylene chloride/methanol. 2.6 g=56.6% of the theoretical yield is obtained as an amorphous solid.

| Analysis: $C_{14}H_{16}F_4N_2O_6$ MW 384.28 | | | | |
|---|---|---|---|---|
| Cld: | C 43.75 | H 4.19 | F 19.77 | N 7.29 | O 24.98% |
| Fnd: | 43.92 | 4.37 | 19.53 | 7.02 | |

Example 39
5-Fluoro-3-(D-gluconamido)-2-hydroxy-benzoic acid-2,2,2-trifluoroethyl)amide

(a)
5-Fluoro-3-(pentaacetoxy-D-gluconamido)-2-hydroxy-benzoic acid-(2,2,2,-trifluoroethyl)amide 4.29 g (17 mmol) of 3-amino-5-fluoro-2-hydroxy-benzoic acid- (2,2,2,-trifluoro-ethyl)amide (Example 37c is dissolved in 40 ml of THF, 2.03 g (20 mmol) of triethylamine and 8.5 g (20 mmol) of pentaacetoxy-D-gluconic acid chloride are added and stirred for 12 hours at room temperature. The reaction mixture is concentrated by evaporation in a vacuum, the residue is dissolved in ethyl acetate and shaken out with water. The organic phase is dried on MgSO$_4$, filtered, concentrated by evaporation and the residue is chromatographed on silica gel 60 with ethyl acetate/hexane. 68.2% of the theoretical yield is obtained as an amorphous solid.

| Analysis: $C_{25}H_{28}F_4N_2O_8$ MW 560.5 | | | | |
|---|---|---|---|---|
| Cld: | C 53.37 | H 5.03 | F 13.55 | N 4.99 | O 22.83% |
| Fnd: | 53.58 | 5.26 | 13.37 | 4.72 | |

(b) 5-Fluoro-3-(gluconamido)-2-hydroxy-benzoic acid-(2,2,2,-trifluoro-ethyl)amide (8.5 mmol) of 5-fluoro-3-(pentaacetoxy-D-gluconamido)-2-hydroxy-benzoic acid-(2,2,2,-trifluoro-ethyl)amide is dissolved in 30 ml of methanol, 10 ml of 1N methanolic NaOH is added and stirred for 1 hour at 40° C. Then 30 ml of cation exchanger Amberlyst 15 is added and stirred for 1 hour at room temperature. The ion exchanger is filtered off, the filtrate is evaporated to dryness, the residue is extracted several times with methylene chloride and then dried in a vacuum at 50° C. 76.3% of the theoretical yield is obtained as an amorphous solid.

| Analysis: $C_{15}H_{18}F_4N_2O_8$ MW 430.31 | | | | |
|---|---|---|---|---|
| Cld: | C 41.86 | H 4.21 | F 17.66 | N 6.51 | O 29.74% |
| Fnd: | 42.07 | 4.42 | 17.49 | 5.32 | |

Example 40
2-[N-(4-fluoro 3 trifluoromethylphenyl)sulfamoyl]-acetic acid-(2,3,4-trihydroxy-butyl)amide

(a)
2-[N-(4-fluoro-3-trifluoromethylphenyl)sulfamoyl]-acetic acid methyl ester Analogously to the instructions for example 7, 5 g (27.64 mmol) of 4-fluoro-3-(trifluoromethyl)-aniline in 25 ml of dry pyridine is reacted with 4.82 g (27.4 mmol) of chlorosulfonyl acetic acid methyl ester in 100 ml of dry dichloroethane. After crystallization from ether/hexane, 7.35 g=84.35% of the theoretical yield is obtained. Melting point 111°-112° C.

(b)
2-[N-(4-Fluoro-3-trifluoromethylphenyl)sulfamoyl]-acetic acid

Analogously to the instructions for Example 8, 2.2 g (6.98 mmol) of 2-[N-(4-fluoro-3-trifluoromethylphenyl)sulfamoyl]-acetic acid methyl ester in dioxane is saponified with aqueous NaOH. After acidification, extraction and crystallization from ethyl acetate/hexane, 1.96 g=93.2% of the theoretical yield of crystals is obtained. Melting point 138°-140° C.

(c) 2-[N-(4-Fluoro-3-trifluoromethylphenyl)sulfamoyl] acetic acid-[2-hydroxy-2-(2,2-dimethyl-1,3-dioxolan-4-yl)-ethylamide]

Analogously to the instructions for Example 9(a), 2.21 g (7 mmol) of 2-[N-(4-fluoro-3-trifluoromethylphenyl)sulfamoyl] acetic acid in dioxane is reacted with 1.13 g (7 mmol) of 2-hydroxy-2-(2,2-dimethyl-1,3-dioxolan-4-yl)-ethylamine for about 1 hour at 90° C. After concentration by evaporation and crystallization from ethanol/ether, 2.87 g=92.3% of the theoretical yield is obtained as a crystallizate. Melting point 144°-146° C.

(d)
2-[N-(4-Fluoro-3-(trifluoromethylphenyl)sulfamoyl]-acetic acid-(2,3,4-trihydroxy-butyl)amide Analogously to the instructions for Example 9(b), 1.8 g (4.05 mmol) of 2-[N-(4-fluoro-3-trifluoromethylphenyl)sulfamoyl]-acetic acid-[2-hydroxy-2-(2,2-dimethyl-1,3-dioxolan-4-yl)-ethylamide] in 10 ml of trifluoroacetic acid is converted to the title compound. After crystallization from ethanol/diethyl ether, 1.3 g=79.4% of the theoretical yield is obtained of hygroscopic crystals.

| Analysis: $C_{13}H_{16}F_4N_2O_6S$ MW 404.45 | | | | | |
|---|---|---|---|---|---|
| Cld: | C 38.61 | H 3.99 | F 18.79 | N 6.93 | O 23.8 | S 7.93% |
| Fnd: | 38.83 | 4.17 | 18.93 | 6.76 | | 7.67 |

Example 41
4
[N-(4-Fluoro-3-trifluoromethylphenyl)sulfamoyl]-benzoic acid-(2,3,4-trihydroxy-butyl)amide

(a)
4-[N-(4-Fluoro-3-trifluoromethylphenyl)sulfamoyl]-benzoic acid

Analogously to Example 10, 2.21 g (10 mmol) of 4-chlorosulfonyl-benzoic acid is reacted with 1.79 g (10 mmol) of 4-fluoro-3-(trifluoromethyl)-aniline in pyridine and the crude product is crystallized from ethanol. 3.3 g=90.84 mmol of crystalline product is obtained. Melting point 238°-241° C.

(b)
4-[N-(4-Fluoro-3-trifluoromethylphenyl)sulfamoyl]-benzoic acid-[2-hydroxy-2-(2,2-dimethyl-1,3-dioxolan-4-yl)-ethylamide]

Analogously to Example 11(a), 3.63 g (10 mmol) of 4-[N-(4-fluoro-3-trifluoromethylphenyl)sulfamoyl)benzoic acid in ethyl acetate with $SOCl_2$ is converted into the acid chloride and the latter is reacted with 1.93 g (12 mmol) of 2-hydroxy-2-(2,2-dimethyl-1,3-dioxolan-4-yl)-ethylamine and the crude product is purified by chromatography. 4.2 g=82.9% of the theoretical yield of the compound is obtained as an amorphous solid.

| Analysis: $C_{21}H_{22}F_4N_2O_6S$ MW 506.47 | | | | | |
|---|---|---|---|---|---|
| Cld: | C 49.8 | H 4.37 | F 15.0 | N 5.53 | O 18.95 | S 6.33% |
| Fnd: | 49.62 | 4.21 | 15.13 | 5.67 | | 6.27 |

(c)
4-[N-(4-Fluoro-3-trifluoromethylphenyl)sulfamoyl]-benzoic acid-(2,3,4-trihydroxybutyl)amide Analogously to Example 11(b), 3.8 g (7.5 mmol) of 4-[N-(4-fluoro-3-trifluoromethylphenyl)sulfamoyl]-benzoic acid-[2-hydroxy-2-(2,2-dimethyl-1,3-dioxolan-4-yl)-ethylamide] in methanol/water with cation exchanger is converted into the title compound. 1.74 g=83% of the theoretical yield is obtained as an amorphous solid.

| Analysis: $C_{18}H_{17}F_4N_2O_6S$ MW 465.4 | | | | | |
|---|---|---|---|---|---|
| Cld: | C 46.45 | H 3.68 | F 16.32 | N 6.01 | O 20.62 | S 6.89% |
| Fnd: | 46.57 | 3.82 | 16.48 | 5.79 | | 7.13 |

Example 42
5-[N (4 Fluoro-3-trifluoromethylphenyl)sulfamoyl]-isophthalic acid-bis(2,3,4-trihydroxy-butyl-amide)

(a)
5-[N-(4-Fluoro-3-trifluoromethylphenyl)sulfamoyl]-isophthalic acid dimethyl ester Analogously to Example 12, 5 g (27.64 mmol) of 4-fluoro-3-(trifluoromethyl)-aniline is reacted with 7.32 g (25 mmol) of 4-chlorosulfonyl-isophthalic acid dimethyl ester and the crude product is purified by chromatography and subsequent crystallization from ethyl acetate. 5.48 g-45.55% of the theoretical yield is obtained. Melting point 123°-124° C.

(b)
5-[N-(4-Fluoro-3-trifluoromethylphenyl)sulfamoyl]-isophthalic acid

Analogously to Example 13, 4.35 g (10 mmol) of 5-[N-(4-fluoro-3-trifluoromethylphenyl)sulfamoyl]-isophthalic acid dimethyl ester is alkalinely saponified and the crude product is crystallized from ethyl acetate/hexane 1:1. 3.49 g=85.6% of the theoretical yield is obtained. Melting point 286°-288° C.

(c)
5-[N-(4-Fluoro-3-trifluoromethylphenyl)sulfamoyl]-isophthalic acid-bis-[2-hydroxy-2-(2,2-dimethyl-1,3-dioxolan-4-yl)-ethylamide]

Analogously to Example 14(a), 4.07 g (10 mmol) of 5-[N-(4-(fluoro-3-trifluoromethylphenyl)sulfamoyl]-isophthalic acid is reacted with 2.42 (15 mmol) of 2-hydroxy-2-(2,2-dimethyl-1,3-dioxolan-4-yl)-ethylamine. The crude product is crystallized from ethyl acetate/hexane. 3.02 g=43.5% of the theoretical yield is obtained as a crystallizate. Melting point 217°-218° C.

(d)
5-[N-(4-Fluoro-3-trifluoromethylphenyl)sulfamoyl]-isophthalic acid- bis(2,3,4-trihydroxybutyl-amide)

Analogously to Example 14(b), 4.86 g (7 mmol) of 5-[N-(4-fluoro-3-trifluoromethylphenyl)sulfamoyl]-isophthalic acid-bis[2-hydroxy-2-(2,2-dimethyl-1,3-dioxolan-4-yl)-ethylamide]in ethanol/water with dilute HCl is converted into the hydroxy compound, desalted with anion exchanger and evaporated to dryness. 3.37 g=78.6% of the theoretical yield is obtained as an amorphous solid.

| Analysis: $C_{23}H_{27}F_4N_3O_{10}S$ MW 613.54 | | | | | |
|---|---|---|---|---|---|
| Cld: | C 45.03 | H 4.44 | F 12.39 | N 6.85 | O 26.08 | S 5.23% |
| Fnd: | 44.92 | 4.28 | 12.18 | 6.97 | | 5.34 |

Example 43

3-Fluoro-6-(trifluoromethylsulfamoyl)-benzoic acid-(2,3,4 trihydroxybutyl)amide (a) 3-Fluoro-6-trifluoromethylsulfamoyl)-benzoic acid methyl ester Analogously to Example 21(a), 3.83 g (20 mmol) of 2-amino-5-fluoro-benzoic acid hydrochloride is reacted with 8.46 g (30 mmol) of trifluoromethanesulfonic acid anhydride, the intermediate acid is converted into the methyl ester and the crude product is purified by chromatography. 3.23 g=53.6% of the theoretical yield is obtained as a mainly crystalline product.

| Analysis: $C_9H_7F_4NO_4S$ MW 301.22 | | | | | |
|---|---|---|---|---|---|
| Cld: | C 35.88 | H 2.34 | F 25.22 | N 4.65 | O 21.24 | S 10.64% |
| Fnd: | 35.57 | 2.22 | 25.48 | 4.44 | | 10.72 |

(b) 3-Fluoro-6-(trifluoromethylsulfamoyl)-benzoic acid

Analogously to Example 21(b), 2.41 g (8 mmol) of 3-fluoro-6-(trifluoromethylsulfamoyl)-benzoic acid methyl ester in aqueous dioxane is saponified with NaOH and isolated. 1.55 g=67.3% of the theoretical yield is obtained as a partially crystalline product.

| Analysis: $C_8H_5F_4NO_4S$ MW 287.19 | | | | | |
|---|---|---|---|---|---|
| Cld: | C 33.45 | H 1.75 | F 26.46 | N 4.87 | O 22.28 | S 11.16% |
| Fnd: | 33.73 | 1.88 | 26.57 | 4.62 | | 11.37 |

(c) 3-Fluoro-6-(trifluoromethylsulfamoyl)-benzoic acid-[2-hydroxy-2-(2,2-dimethyl-1,3-dioxolan-4-yl)-ethylamide]

Analogously to Example 22(a), 4.31 g (15 mmol) of 3-fluoro-6-(trifluoromethylsulfamoyl)-benzoic acid is reacted with 3.22 g (20 mmol) of 2-hydroxy-2-(2,2-dimethyl-1,3-dioxolan-4-yl)-ethylamine and the crude product is purified by chromatography on silica gel with ethyl acetate/hexane. 4.93 g=76.3% of the theoretical yield is obtained as an amorphous solid.

| Analysis: $C_{15}H_{18}F_4N_2O_6S$ MW 430.77 | | | | | |
|---|---|---|---|---|---|
| Cld: | C 41.86 | H 4.21 | F 17.65 | N 6.5 | O 22.3 | S 7.45% |
| Fnd: | 42.07 | 4.33 | 17.52 | 6.67 | | 7.27 |

(d) 3-Fluoro-6-(trifluoromethylsulfamoyl)-benzoic acid-(2,3,4-trihydroxy-butyl)amide Analogously to Example 22(b), 5.38 g (12.5 mmol) of 3-fluoro-6-(trifluoromethylsulfamoyl)-benzoic acid-[2-hydroxy-2-(2,2-dimethyl-1,3-dioxolan-4-yl)-ethylamide] is converted to the title compound. 3.52 g–72.3% of the theoretical yield is obtained as an amorphous solid.

| Analysis: $C_{12}H_{13}F_4N_2O_6S$ MW 389.3 | | | | | |
|---|---|---|---|---|---|
| Cld: | C 37.02 | H 3.36 | F 19.52 | N 7.19 | O 24.65 | S 8.23% |
| Fnd: | 36.87 | 3.6 | 19.75 | 7.32 | | 7.96 |

Example 44

3-Fluoro-6-(trifluoromethylsulfamoyl) benzoic acid-(2,3,4-trihydroxy N-methyl-butyl)amide (a) 3-Fluoro-6-(trifluoromethylsulfamoyl)-benzoic acid-[2-hydroxy-2-(2,2-dimethyl-1,3-dioxolan-4-yl)-ethyl-N-methyl-amide]

Analogously to Example 22(a), 4.31 g (15 mmol) of 3-fluoro-6-(trifluoromethylsulfamoyl)-benzoic acid is reacted with 3.22 g (20 mmol) of 2-methylamino-1-(2,2-dimethyl-1,3-dioxolan-4-yl)-ethanol and the crude product is purified by chromatography on silica gel with ethyl acetate/hexane. 4.93 g=76.3% of the theoretical yield is obtained as an amorphous solid.

| Analysis: $C_{16}H_{20}F_4N_2O_6S$ MW 444.4 | | | | | |
|---|---|---|---|---|---|
| Cld: | C 43.24 | H 4.53 | F 17.10 | N 6.3 | O 21.6 | S 7.21% |
| Fnd: | 42.06 | 4.33 | 17.38 | 6.54 | | 7.27 |

(b) 3-Fluoro-6-(trifluoromethylsulfamoyl)-benzoic acid-(2,3,4-trihydroxy-N-methyl-butyl)amide Analogously to Example 22(b), 3.11 g (7 mmol) of 3-fluoro-6-(trifluoromethylsulfamoyl)-benzoic acid-[2-hydroxy-2-(2,2-dimethyl-1,3-dioxolan-4-yl)-ethyl-N-methyl-amide in aqueous methanol with ion exchanger is converted to the titel compound. 2.32 g=82.3% of the theoretical yield is obtained as a amorphous solid.

| Analysis: $C_{13}H_{15}F_4N_2O_6S$ MW 403.33 | | | | | |
|---|---|---|---|---|---|
| Cld: | C 38.71 | H 3.74 | F 18.84 | N 6.94 | O 23.8 | S 7.95% |
| Fnd: | 38.52 | 3.95 | 18.59 | 7.13 | | 7.68 |

Example 45

Production of a solution of 2-[N-(4-fluoro-3-(trifluoromethylphenyl)sulfamoyl]-acetic acid-(2,3,4-trihydroxy-butyl-amide)

202.225 g (0.5 mmol) of the compound described in Example 40(d) is dissolved in 600 ml of water p.i., 1.211 g of tromethamine and 100 mg of CaNa₂ EDTA are added. It is adjusted to pH 7.2 with 1N HCl, water p.i. is poured in to make 1000 ml, the solution is filtered, poured into Multivials and sterilized by heat.

Example 46

Production of a solution of 5-[N-(4-fluoro-3-(trifluoromethylphenyl)sulfamoyl]-isophthalic acid-bis(2,3,4-trihydroxy-butyl-amide)

306.77 g (0.5 mol) of the compound described in Example 42(b) is dissolved in 600 ml of water p.i. The solution is sterilized by filtering and poured into Multivials and/or ampules.

Example 47

Production of a solution of 5-[N-(4-fluoro-2-trifluoromethylphenyl)sulfamoyl]-isophthalic acid 203.645 g (0.5 mol) of the compound described in Example 13 is suspended in 500 ml of water p.i.. By addition of 5-normal sodium hydroxide solution a solution is produced which is then adjusted to pH 7.2 with 0.1-normal sodium hydroxide solution. After addition of 100 mg of CaNa₂EDTA, water p.i. is poured in to make 1000 ml, it is filtered, poured into Multivials and-/or ampules and sterilized by heat.

Example 48

4-[N-(4-Fluoro-3-(trifluoromethylphenyl)-sulfamoyl]-benzoic acid-(2,3-dihydroxy-I-hydroxymethyl-propyl) amide

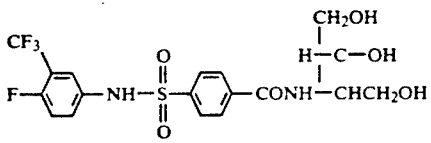

(a) 4-[N-(4-Fluoro-3-(trifluoromethylphenyl)-sulfamoyl)-benzoic acid-(6-hydroxy-2,2-dimethyl-1,3-dioxepan-5-yl)-amide

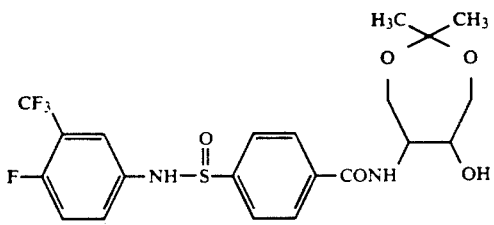

3 g (8.26 mmol) of 4-[N-(fluoro-3-(trifluoromethylphenyl)sulfamoyl] benzoic acid (Example 1a) is added to 160 ml of dimethylformamide and mixed with 1.27 g (8.26 mmol) of hydroxybenzotriazole as well as 1.33 g (8.26 mmol) of 6-amino-2,2-dimethyl-1,3-dioxepan-5-ol (EP No. 0 033 426) with stirring. It is cooled to −10° C., mixed with 1.7 g (8.26 mmol) of dicyclohexylcarbodiimide, left for 1 hour at this temperature and stirred for 72 hours more at room temperature. It is suctioned off over a glass fiber filter, evaporated to dryness in a vacuum and the residue s taken up in ethyl acetate. After washing with sodium bicarbonate solution and water, the solution is dried on sodium sulfate and evaporated to dryness. The residue is purified by chromatography on silica gel. 3.64 g=87% of the theoretical yield is obtained of the compound as an amorphous solid.

| Analysis: $C_{21}H_{22}F_4N_2O_6S$ MW 506.47 | | | | | |
|---|---|---|---|---|---|
| Cld: | C 49.8 | H 4.38 | F 15.0 | N 5.53 | O 18.95 | S 6.33% |
| Fnd: | 49.91 | 4.46 | 14.87 | 5.67 | | 6.22 |

(b)
4-[N-(4-Fluoro-3-trifluoromethylphenyl)-sulfamoyl]-benzoic acid-(2,3-dihydroxy-1-hydroxymethyl-propyl)-amide

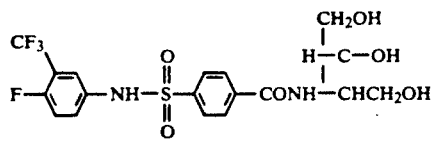

2 g (3.95 mmol) of 4-[N-(4-fluoro-3-trifluoromethylphenyl)sulfamoyl]-benzoic acid-(6-hydroxy-2,2-dimethyl-1,3-dioxepan-5-yl)-amide as well as 2 ml of cation exchanger in H. form are added to a solution of 10 ml of ethanol and 5 ml of distilled water and warmed for 90 minutes on the water bath. It is filtered from the exchanger, rewashed with distilled water, evaporated to dryness in a vacuum, and again taken up in water and by freeze-drying of this solution, 1.55 g=84.2% of the theoretical yield is obtained as an amorphous solid.

| Analysis: $C_{18}H_{18}F_4N_2O_6S_1$ MW 466.4 | | | | | | |
|---|---|---|---|---|---|---|
| Cld: | C 46.36 | H 3.89 | F 16.29 | N 6.01 | O 20.58 | S 6.87% |
| Fnd: | 46.27 | 4.02 | 16.3 | 5.83 | | 6.68% |

Example 49

Performance of in vivo $^{19}F$ NMR spectroscopic pH determinations with 5-[N-(4-fluoro-2-trifluoromethylphenyl)sulfamoyl]-isophthalic acid (Example 13)

An aqueous solution of the fluorocompound is produced with a concentration of 0.4 mol/l. The pH of the aqueous solution is adjusted with NaOH to 7.2.

The NMR spectra are measured with an animal experimental nuclear spin tomograph (General Electric), which operates with a field strength of 2 tesla (corresponds to an RF resonance frequency of 80.5 MHz). The signals can be picked up by the whole-body coil (animal size) or surface coils.

The experiments are performed with female rats of the Wistar-Han-Schering strain (SPF) with a body weight of 200 g. The animal is anesthetized by an intramuscular injection of Rompun/Ketavet (1:1, 1 ml/kg of body weight). Then a butterfly needle is placed in the animal in one of the tail veins. The animal is placed in a whole-body coil and the latter is tuned to the fluororesonance frequency. The spectrum of the entire animal is developed with this coil, i.e., no volume-selective spectroscopy is performed.

The fluorinated compound is applied intravenously within 30 seconds in a dose of 0.5 mmol/kg and an F spectrum is registered within 4 minutes.

FIG. 1 shows the fluorospectrum, which was obtained 5 minutes after application. The spectrum consists of 3 signals, and the most intense signal corresponds to the signal of the $CF_3$ group, the reference signal. The two signals in the aromatic range shows the fluorocompound is in 2 environments with different pHs. The pHs are calculated from the chemical shifts to 6.5 and 7.7.

Figure 2:
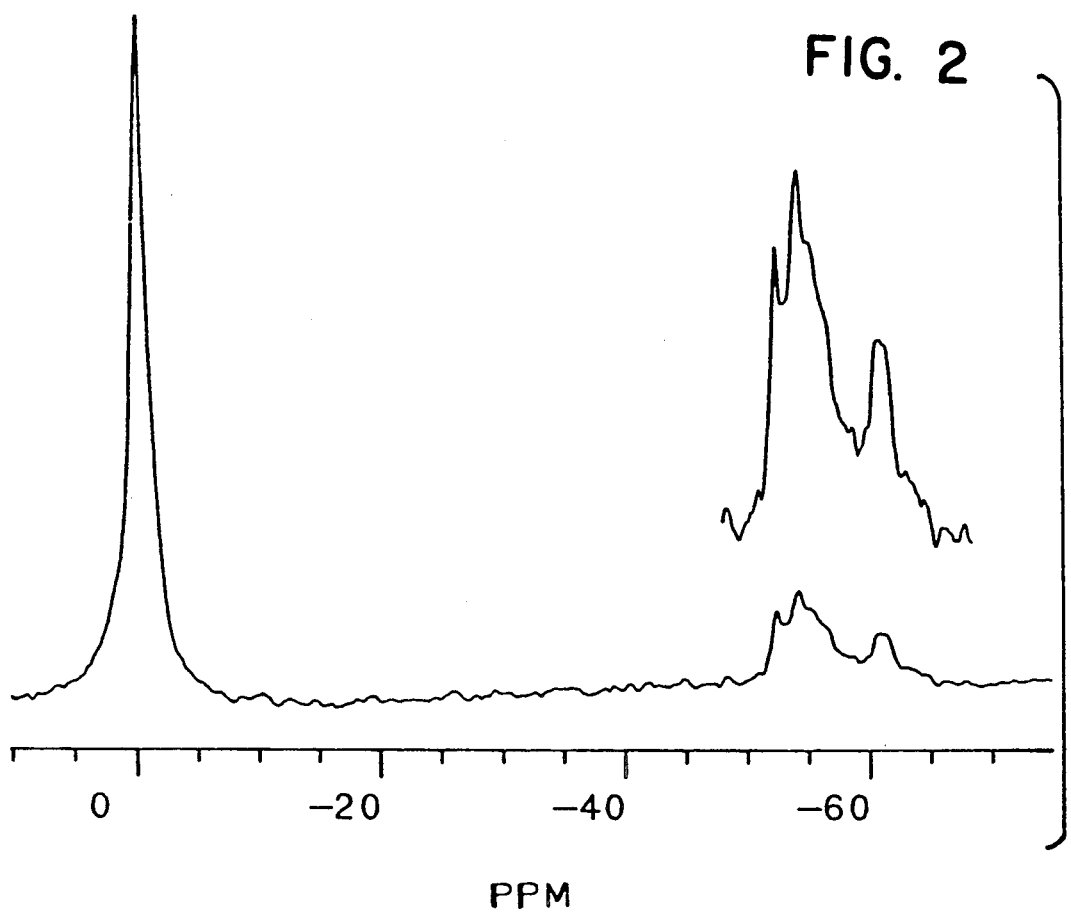

50 minutes after application (FIG. 2) the signal from the alkaline range has almost disappeared, while the signal in the acid range was split into several signals. This spectrum shows that the compound which at the beginning of the experiment was found only in the blood, was distributed extravascularly, and that the different areas in the tissue show different pHs. The areas correlate with the extracellular space, intracellular space (in this case especially intracellular distribution in the cells of the renal parenchyma) as well as areas of the renal parenchyma, the ureter and bladder.

Figure 3:
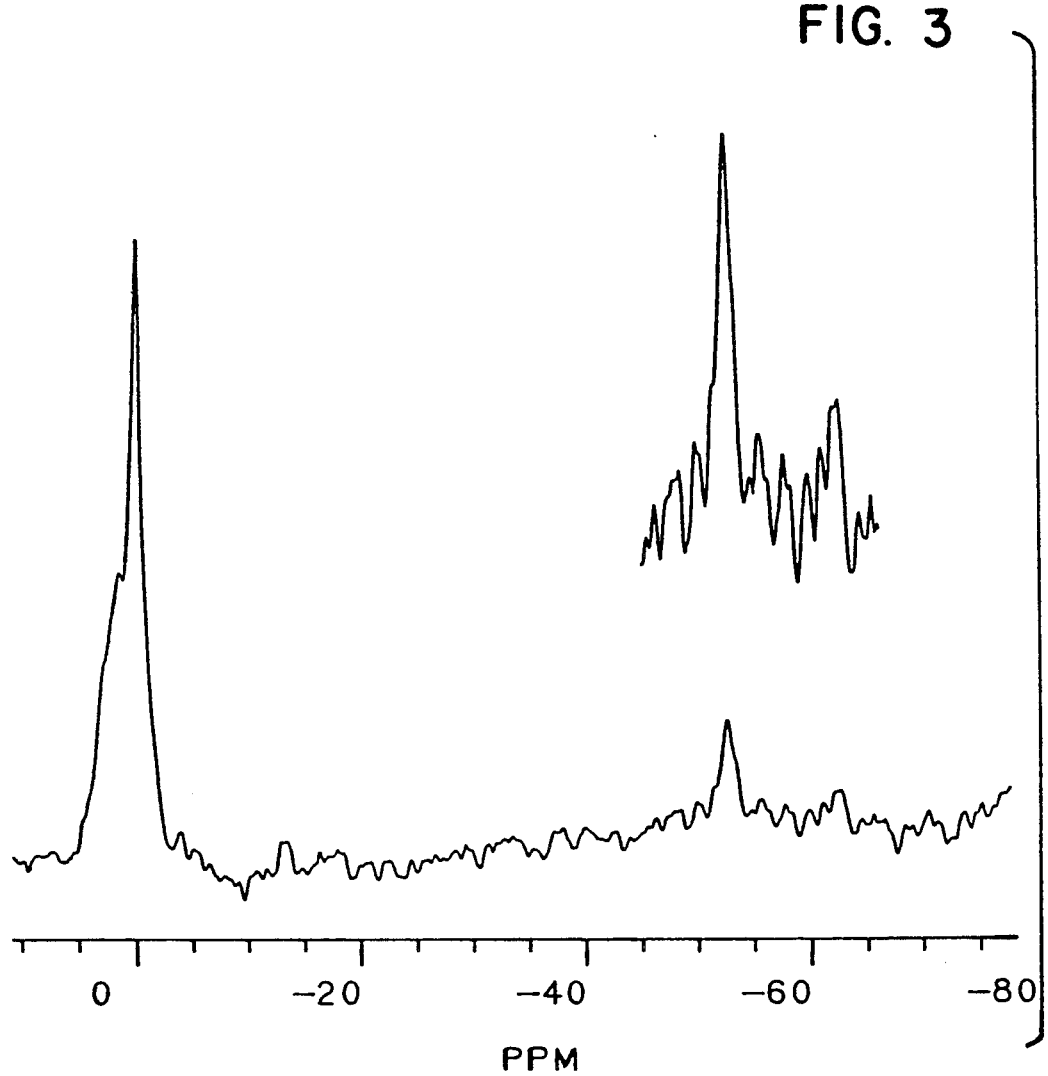

After measurement of the total animal, the animal was removed from the coil and positioned on a surface coil so that the bladder area was picked up by the coil. FIG. 3 shows this volume-selective spectrum, which was obtained in 20 minutes measuring time. The intense signals originate from the fluorocompound in the bladder. The chemical shift in the aromatic range is identical with the deep-field signal of the aromatic range in FIG. 2. This spectrum shows that the compound is renally excreted and the lowest (most acid) pH is in the bladder in the animal.

Example 50

Performance of $^{19}F$ imaging

Production of the solution of the fluorinated substance as well as preparation of the animal take place as in taking the $^{19}F$ NMR spectra.

Figure 4:
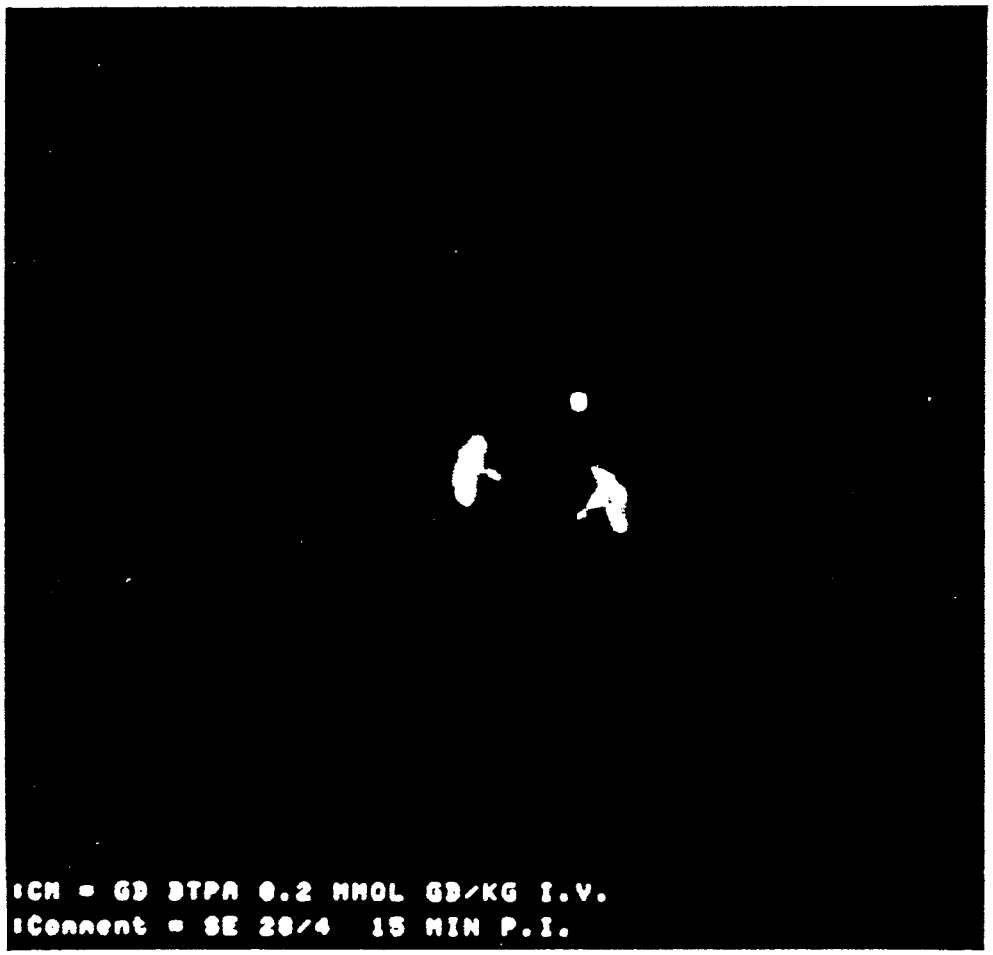
FIG. 4 relates to Example 50 and is the projection $^{19}F$ image of the kidney, bladder, and ureters of a rat administered 0.75 mmol/kg of 5-[N-4-fluoro-2-trifluoromethylphenyl)sulfamoyl] isophthalic acid and 0.2 mmol/kg GdDTPA.

The test animal is placed in the measuring coil and the fluorinated compound is applied in a dose of 0.75 mmol/kg of body weight by the tail vein in 1 minute. Then an intravenous application takes place, also by needle in the tail vein, of GdDTPA in a dose of 0.2 mmol/kg. Making of the image takes place with a projection spin echo sequence and the parameters: TR=28 msec (repetition rate), TE=4 msec (echo time), NEX=256 (number of averagings); the total measuring time is 15 minutes. The image (FIG. 4) shows the kidney, bladder and ureter, since the examined compound is renally excreted and a high F concentration is reached by reabsorption of water in these areas.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a method of F-NMR imaging comprising administering an effective amount of an imaging agent to a subject, the improvement wherein said imaging agent is a fluorosubstituted benzene derivative of Formula I

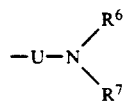

(I)

wherein
Y is OH or $-NHSO_2R^1$
wherein
$R^1$ is

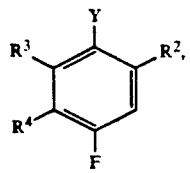

or a straight-chain or branched-chain $C_{1-10}$-alkylene, optionally substituted by 1 to 6 fluorine atoms, each terminating in a fluorine atom or a radical —V, V independently stands for H, $-U-OR^5$ or

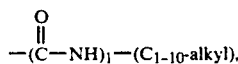

wherein
U is CO or $SO_2$,
$R^5$ is H, a saturated, unsaturated, straight-chain or branched-chain or cyclic $C_{1-16}$ hydrocarbon radical, optionally substituted by 1 to 6 hydroxy groups,
$R^6$ and $R^7$, each independently are H, a straight-chain or branched-chain $C_{1-16}$-hydrocarbon, optionally substituted by 1 to 6 hydroxy groups or 1 to 12 fluorine atoms, or
$R^6$ and $R^7$ together with the nitrogen atom are a saturated five- or six-membered heterocyclic ring, optionally containing another heteroatom,
$X^1$ and $X^2$ each independently stand for fluorine, —V, a straight-chain or branched-chain $C_{1-10}$-alkylene, optionally substituted by 1 to 6 fluorine atoms, and terminating in a fluorine atom or —V, or $-N(R^6)-CO-R^8$,
wherein $R^8$ is a straight-chain or branched-chain $C_{1-16}$-hydrocarbon optionally substituted by 1 to 6 hydroxy groups and optionally substituted by 1 to 12 fluorine atoms and optionally interrupted by 1 to 3 oxygen atoms;
m is 0, 1, 2, 3 or 4,
n is 0 or 1, and
n and m do not simultaneously mean 0;
$R^2$ is hydrogen, fluorine, $-N(R^6)-CO-R^8$, a straight-chain or branched-chain $$-(C-NH)_l-(C_{1-10}\text{-alkyl}),$$
$$\phantom{-(}\|\phantom{C-NH)_l-(C_{1-10}\text{-alkyl}),}$$
$$\phantom{-(C-NH}O$$

optionally substituted with 1 to 6 fluorine atoms, and l stands for the numbers 0 or 1, or

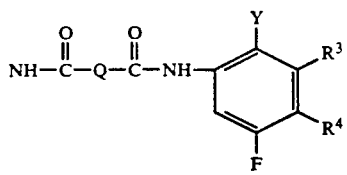

wherein Q is $-(CF_2)_k-$ or $-(C_6F_4)-$
wherein k is 1, 2, 3, 4, 5, or 6;
$R^3$ and $R^4$ each independently are H, fluorine, a straight-chain or branched-chain $C_{1-10}$-alkyl optionally substituted by 1 to 6 fluorine atoms, —V or $-N(R^6)-CO-R^8$;
provided that at least two fluorine atoms are present in the molecule, or
a physiologically acceptable salt thereof with an organic or inorganic base.

2. A method of claim 1, wherein Y is OH.

3. A method of claim 1, wherein Y is $NHSO_2R^1$.

4. A method of claim 3, wherein $R^1$ is a straight-chain or branched-chain $C_{1-10}$-alkylene, optionally substituted by 1-6 fluorine atoms, terminating in a fluorine atom or a radical-V.

5. A method of claim 3, wherein $R^1$ is

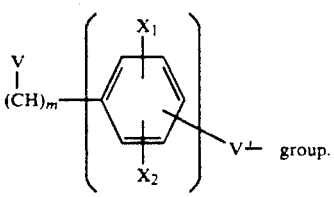

6. A method of claim 3, wherein at least one V is independently U-OR$^5$.

7. A method of claim 3, wherein at least one V is

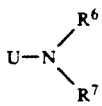

8. A method of claim 3, wherein U is C=O.
9. A method of claim 3, wherein U is SO$_2$.
10. A method of claim 6, wherein R$^5$ is H.
11. A method of claim 6, wherein U is N-(2,3,4-trihydroxyl-butyl)amide.
12. A method of claim 1, wherein R$^2$ is

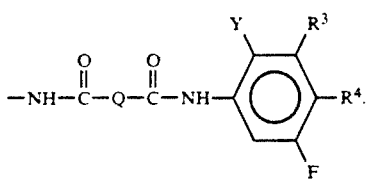

13. A method of claim 1, further comprising administering a paramagnetic compound.

14. A method of claim 1, wherein the compound is coupled to an antibody.

15. A method of claim 13, wherein the paramagnetic compound is in the form of a complex of a paramagnetic compound and a chelating agent.

16. A method of claim 1, wherein, in the compound, Y is OH.

17. A method of claim 1, wherein, in the compound, V in the

group in R$^1$ is H.

18. A method of claim 17, wherein in the compound, another V in R$^1$ is

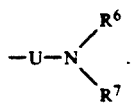

19. A method of claim 1, wherein, in the compound, R$^1$ is C$_{1-10}$-alkylene, optionally substituted by 1-6 fluorine atoms.

20. A method of claim 1, wherein, in the compound, R$^5$ is a C$_{1-16}$ hydrocarbon radical.

21. In a method of non-invasively measuring pH in living tissue in a subject, the improvement comprising administering to said subject an effective amount of a fluorosubstituted benzene derivative of Formula I

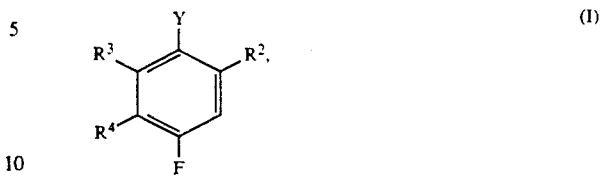

wherein
Y is OH or —NHSO$_2$R$^1$ wherein
R$^1$ is

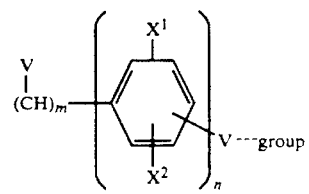

or a straight-chain or branched -chain C$_{1-10}$-alkylene, optionally substituted by 1 to 6 fluorine atoms, each terminating in a fluorine atom or a radical —V, V independently stands for H, —U—OR$^5$ or

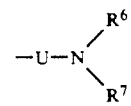

wherein
U is CO or SO$_2$,

R$^5$ is H, a saturated, unsaturated, straight-chain or branched-chain or cyclic C$_{1-16}$ hydrocarbon radical, optionally substituted by 1 to 6 hydroxy groups, R$^6$ and R$^7$, each independently are H, a straight-chain or branched-chain C$_{1-16}$-hydrocarbon, optionally substituted by 1 to 6 hydroxy groups or 1 to 12 fluorine atoms, or R$^6$ and R$^7$ together with the nitrogen atom are a saturated five- or six-membered heterocyclic ring, optionally containing another heteroatom, X$^1$ and X$^2$ each independently stand for fluorine, —V, a straight-chain or branched-chain C$_{1-10}$-alkylene, optionally substituted by 1 to 6 fluorine atoms, and terminating in a fluorine atom or —V, or —N(R$^6$)—CO—R$^8$, wherein R$^8$ is a straight-chain or branched-chain C$_{1-16}$-hydrocarbon optionally substituted by 1 to 6 hydroxy groups and optionally substituted by 1 to 12 fluorine atoms and optionally interrupted by 1 to 3 oxygen atoms;

m is 0, 1, 2, 3 or 4,
n is 0 or 1, and
n and m do not simultaneously mean 0;
R$^2$ is hydrogen, fluorine, —N(R$^6$)—CO—R$^8$, a straight-chain or branched-chain

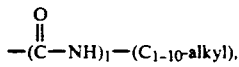

optionally substituted with 1 to 6 fluorine atoms, and l stands for the numbers 0 or 1, or

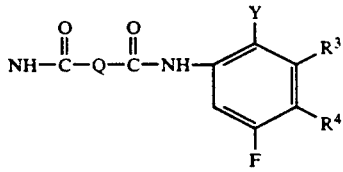

wherein Q is —(CF$_2$)$_k$— or —(C$_6$F$_4$)—
wherein k is 1, 2, 3, 4, 5, or 6;
R$^3$ and R$^4$ each independently are H, fluorine, a straight-chain or branched-chain C$_{1-10}$-alkyl optionally substituted by 1 to 6 fluorine atoms, —V or —N(R$^6$)—CO—R$^8$;

provided that at least two fluorine atoms are present in the molecule, or
a physiologically acceptable salt thereof with an organic or inorganic base.

22. A method of claim 21, wherein, in the compound, Y is OH.

23. A method of claim 21, wherein, in the compound, V in the —(CH)$_m$— group in R$^1$ is H.

24. A method of claim 23, wherein in the compound, another V in R$^1$ is

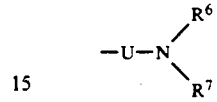

25. A method of claim 21, wherein, in the compound, R$^1$ is C$_{1-10}$-alkylene, optionally substituted by 1-6 fluorine atoms.

26. A method of claim 21, wherein, in the compound, R$^5$ is a C$_{1-16}$ hydrocarbon radical.

* * * * *